US011077212B2

(12) United States Patent
Morse et al.

(10) Patent No.: US 11,077,212 B2
(45) Date of Patent: Aug. 3, 2021

(54) MOLECULAR IMAGING OF CANCER CELLS IN VIVO

(75) Inventors: David L. Morse, Tampa, FL (US); Robert J. Gillies, Tampa, FL (US); William Bradford Carter, Tampa, FL (US); Narges K. Tafreshi, Tampa, FL (US); Marilyn M. Bui, Tampa, FL (US); Steven A. Enkemann, Lutz, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 304 days.

(21) Appl. No.: 13/813,605

(22) PCT Filed: Aug. 24, 2011

(86) PCT No.: PCT/US2011/048995
§ 371 (c)(1),
(2), (4) Date: Jan. 31, 2013

(87) PCT Pub. No.: WO2012/027493
PCT Pub. Date: Mar. 1, 2012

(65) Prior Publication Data
US 2013/0129619 A1    May 23, 2013

Related U.S. Application Data

(60) Provisional application No. 61/402,098, filed on Aug. 24, 2010, provisional application No. 61/424,992, filed on Dec. 20, 2010.

(51) Int. Cl.
*A61K 49/00* (2006.01)
*A61K 51/10* (2006.01)

(52) U.S. Cl.
CPC ...... *A61K 49/0058* (2013.01); *A61K 49/0002* (2013.01); *A61K 51/1045* (2013.01)

(58) Field of Classification Search
None
See application file for complete search history.

(56) References Cited

U.S. PATENT DOCUMENTS

| | | | |
|---|---|---|---|
| 5,530,101 A | 6/1996 | Queen | |
| 5,579,250 A | 11/1996 | Balaji | |
| 5,585,089 A | 12/1996 | Queen | |
| 5,612,895 A | 3/1997 | Balaji | |
| 5,631,280 A | 5/1997 | Ciccarone | |
| 5,693,762 A | 12/1997 | Queen | |
| 6,180,370 B1 | 1/2001 | Queen | |
| 6,407,213 B1 | 6/2002 | Carter | |
| 2003/0045468 A1 | 3/2003 | Fling | |
| 2009/0234225 A1* | 9/2009 | Martin | G01N 21/6428 600/431 |

FOREIGN PATENT DOCUMENTS

| | | |
|---|---|---|
| WO | 2007065027 | 6/2007 |
| WO | 2010147666 | 12/2010 |

OTHER PUBLICATIONS

Chrastina et al. Biodistribution and pharmacokinetics of 125I-labeled monoclonal antibody M75 specific for carbonic anhydrase IX, an intrinsic marker of hypoxia, in nude mice xenografted with human colorectal carcinoma. 2003 Int. J. Cancer 105: 873-881.*
Michal et al. Renal angiomyoadenomatous tumor: morphologic, immunohistochemical, and molecular genetic study of a distinct entity. 2009 Virchows Arch. 454: 89-99. Published online Nov. 20, 2008.*
Paudyal et al. Dual functional molecular imaging probe targeting CD20 with PET and optical imaging. 2009 Oncol. Rep. 22: 115-119.*
Brouwers et al. PET radioimmunoscintigraphy of renal cell cancer using 89Zr-labeled cG250 monoclonal antibody in nude rats. 2004 Cancer Biother. Radiopharm. 19: 155-163.*
Parkkila et al. Expression of the membrane-associated carbonic anhydrase isozyme XII in the human kidney and renal tumors. 2000 J. Histochem. Cytochem. 48: 1601-1608.*
Kobayashi et al. New strategies for fluorescent probe design in medical diagnostic imaging. 2010 Chem. Rev. 110: 2620-2640.*
Ljungberg et al. Renal cell carcinoma guideline. 2007 Eur. Urol. 51: 1502-1510.*
Leppert et al. Carbonic anhydrase IX and the future of molecular markers in renal cell carcinoma. 2005 BJU Int. 96: 281-285.*
Swinson et al. Carbonic anhydrase IX expression, a novel surrogate marker of tumor hypoxia, is associated with a poor prognosis in non-small-cell lung cancer. 2003 J. Clin. Oncol. 21: 473-482.*
Veiseh et al. Tumor paint: a chlorotoxin:Cy5.5 bioconjugate for intraoperative visualization of cancer foci. 2007 Cancer Res. 67: 6882-6888. (Year: 2007).*
Barrett et al. In vivo diagnosis of epidermal growth factor receptor expression using molecular imaging with a cocktail of optically labeled monoclonal antibodies. 2007 Clin. Cancer Res. 13: 6639-6648. (Year: 2007).*
Product information for catalog # MAB2188, monoclonal anti-human carbonic anhydrase IX antibody. R&D Systems, Inc. Published Jul. 27, 2009. 1 page. (Year: 2009).*
New product booklet. R&D Systems, Inc. Published Jun. 2007. 12 pages. (Year: 2007).*
Sampath et al. Near infrared fluorescent optical imaging for nodal staging. 2008 J. Biomed. Opt. 13: 041312; 10 pages. (Year: 2008).*
Achilefu, et al., "Optical imaging of mammaglobin expression in breast cancer", URL:http//www.dtic.mil/dtic/tr/fulltext/u2/a456599., retrieved on May 1, 2006.

(Continued)

*Primary Examiner* — Jennifer Lamberski
(74) *Attorney, Agent, or Firm* — Pabst Patent Group LLP

(57) ABSTRACT

Cellular targets on cancer cells have been identified that can be used with targeted molecular imaging to detect the cancer cells in vivo. Non-invasive methods for detecting cancer cells, such as metastasized cancer cells, are therefore provided. Also provided are compositions and kits for use in the disclosed methods.

11 Claims, 11 Drawing Sheets

Specification includes a Sequence Listing.

(56) References Cited

OTHER PUBLICATIONS

Baggett, et al., "Thermostability of firefly luciferases affects efficiency of detection by in vivo bioluminescence", Mol Imaging 3:324-32 (2004).
Brennan, et al., "CA IX is an independent prognostic marker in premenopausal breast cancer patients with one to three positive lymph nodes and a putative marker of radiation resistance", Clin Cancer Res 12:6421-31 (2006).
Chia, et al., "Prognostic significance of a novel hypoxia-regulated marker, carbonic anhydrase IX, in invasive breast carcinoma", J Clin Oncol 19:3660-8 (2001).
Colpaert, et al., "The presence of a fibrotic focus in Invasive breast carcinoma correlates with the expression of carbonic anhydrase IX and is a marker of hypoxia and poor prognosis", Breast CancerRes Treat 81:137-147 (2003).
Divgi, et al., "Preoperative characterisation of clear-cell renal carcinoma using iodine-124-labelled antibody chimeric G250 (124l-cG250) and PET in patients with renal masses: a phase I trial", Lancet Oncology, 8(4):304-10 (2007).
Goonewardene, et al., "Hypoxia-induced pathways in breast cancer", Microsc Res Tech 59:41-8 (2002).
Hussain, et al., "Hypoxia-regulated carbonic anhydrase IX expression is associated with poor survival in patients with invasive breast cancer", Br J Cancer 96:104-9 (2007).
Ivanov, et al., "Expression of hypoxia-inducible cell-surface transmembrane carbonic anhydrases in human cancer", Am J Pathol 158:905-19 (2001).
Lancashire, et al., "A validated gene expression profile for detecting clinical outcome in breast cancer using artificial neural networks", Breast Cancer Res Treat 120:83-93 (2010).
Li, et al., "Expression and activity of carbonic anhydrase IX is associated with metabolic dysfunction in MDA-MB-231 breast cancer cells", Cancer Invest 27:613-623 (2009).
Morse, et al., "Determining suitable internal standards for mRNA quantification of increasing cancer progression in human breast cells by real-time reverse transcriptase polymerase chain reaction", Anal Biochem 342:69-77 (2005).
Robey, et al., "Hypoxia-inducible factor-1alpha and the glycolytic phenotype in tumors", Neoplasia 7:324-30 (2005).
Schlauder, et al., "Assessment of muscarinic and nicotinic acetylcholine receptor expression in primitive neuroectodermal tumor/ewing family of tumor and desmoplastic small round cell tumor an immunohistochemical and Western blot study of tissue microarray and cell lines", Fetal Pediatr Pathol 27:83-97 (2008).
Sevick-Muraca, et al., "Imaging of lymph flow in breast cancer patients after microdose administration of a near-infrared fluorophore: feasibility study", Radiology 246:734-41 (2008).
Sharma, et al., "Gold-Speckled Multimodal Nanoparticles for Non-invasive Bioimaging", Chem Mater 20:6087-94 (2008).
Span, et al., "Carbonic anhydrase-9 expression levels and prognosis in human breast cancer: association with treatment outcome", Br J Cancer, 89:271-6 (2003).
Sprague, et al., "In vitro and in vivo investigation of matrix metalloproteinase expression in metastatic tumor models", Nuclear Med. Biol., 33(2):227-37 (2006).
Supuran, "Development of small molecule carbonic anhydrase IX inhibitors", Br J Urology Intl., 101(54):39-40 (2008).
Supuran, et al., "Carbonic anhydrases as targets for medicinal chemistry", Bioorg Med Chem., 15:4336-50 (2007).
Tafreshi, et al., "A mammaglobin-A targeting agent for noninvasive detection of breast cancer metastasis in lymph nodes", Lymph Cancer Res., 71(3):1050-9 (2010).
Trastour, et al., "HIF-1alpha and CA IX staining in invasive breast carcinomas: prognosis and treatment outcome", Int J Cancer 120:1451-1458 (2007).
Watson, et al., "Mammaglobin expression in primary, metastatic, and occult breast cancer", Cancer Res., 59(13):3028-31 (1999).

* cited by examiner

MOLECULAR IMAGING OF CANCER CELLS IN VIVO

CROSS REFERENCE TO RELATED APPLICATIONS

This application claims benefit of U.S. Provisional Application No. 61/402,098, filed Aug. 24, 2010, and U.S. Provisional Application Ser. No. 61/424,992, filed Dec. 20, 2010. U.S. Provisional Application No. 61/402,098, filed Aug. 24, 2010, and U.S. Provisional Application Ser. No. 61/424,992, filed Dec. 20, 2010, are hereby incorporated herein by reference in their entirety.

STATEMENT REGARDING FEDERALLY SPONSORED RESEARCH

This invention was made with Government Support under Agreements R01 CA97360 and R01 CA123547 awarded to Robert J. Gillies by the National Institutes of Health (NIH). The Government has certain rights in the invention.

REFERENCE TO SEQUENCE LISTING

The Sequence Listing submitted Jan. 31, 2013 as a text file named "MOF_10MA024_AMD_AFD_Sequence_Listing_Text_File.txt," created on Jan. 31, 2013 and having a size of 1,256 bytes is hereby incorporated by reference pursuant to 37 C.F.R. § 1.52(e)(5).

FIELD OF THE INVENTION

This invention is generally related to cancer screening. More specifically, this invention relates to the use of targeted molecular imaging to detect cancer in vivo.

BACKGROUND OF THE INVENTION

Around most small cancers there is an area where microscopic sized cancers cells have spread out or migrated. Normally a surgeon tries to remove the tumor with a rim of normal tissue so that he is sure of removing these small cells as well. If cancer cells are found right up to the edge of the resected tissue, this is referred to as having cancer at the margin (or positive margins). Cancer patients have a reduced chance of cancer recurrence if resection margins are negative. Current techniques to assess surgical margins involve post-operative evaluation of pathology specimens collected during surgery. If the pathology specimen is positive, additional surgery may be required. Therefore, a method to intraoperative assess the resection margin prior to actual resection will minimize the chance of a positive microscopic margin and minimize the need for additional surgery.

In addition, determining the presence or absence of axillary lymph nodal metastasis is critical to the pathologic staging, prognostication and guidance of treatment in patients with certain cancers, such as breast cancer (Stacker, S. A., et al. *Nat Rev Cancer* 2:573-583 (2002); Tafreshi, N. K., et al. *Cancer Control* 17:143-155 (2010)). The sentinel lymph node (SLN) is the axillary node that first receives drainage from the breast parenchyma in the area of the primary tumor and, therefore has the highest probability of containing metastatic cells. SLNs can be identified by a surgical application referred to as intraoperative lymphatic mapping (ILM or SLN mapping). ILM helps trace the lymphatic drainage patterns in a cancer patient to evaluate potential tumor drainage and cancer spread in lymphatic tissue. The ILM technique does not detect cancer; rather it helps surgeons identify the lymph node(s) to which a tumor is likely to drain and spread. ILM involves peritumoral injection of a radioactive tracing agent to identify SLNs, which are then biopsied for pathological examination (Albertini, J. J., et al. *JAMA* 276:1818-1822 (1996); Giuliano, A. E. et al. *Annals of Surgery* 220:391-401 (1994); Krag, D. N. et al. *Surg Oncol* 2:335-340 (1993)). The sulfer colloid of technetium 99m ($^{99m}$Tc) is a radioactive tracing agent particularly suited for ILM. Moreover, the radioactive tracing agent Lymphoseek® (Tilmanocept) described in U.S. Pat. No. 6,409,990 is designed to accumulate in lymphatic tissue by specifically binding to mannose binding receptor (MBR; CD206) proteins that reside on the surface of resident dendritic cells and macrophages. If biopsied SLNs are negative for cancer, then complete axillary lymph node dissection can be avoided (Douglas-Jones, A. G. et al. *Histopathology* 55:107-113 (2009)).

However, a limitation of ILM techniques is the lack of biomarkers for targeting these agents to cancer cells. Instead, such agents distribute non-specifically across SLNs providing only an anatomic and non-functional map (Galanzha, E. I. et al. *J Biophotonics* 2:528-539 (2009); McElroy, M. et al. *J Surg Res* 151:68-73 (2009)). As a result, SLN biopsy is required to identify potential cancer cells. SLN biopsy is an invasive surgical procedure, requiring a multi-disciplinary team with specialized imaging and surgical equipment (Douglas-Jones, A. G. et al. *Histopathology* 55:107-113 (2009); Krag, D. et al. *N Engl J Med* 339:941-946 (1998); McMasters, K. M. et al. *J Clin Oncol* 18:2560-2566 (2000); Ung, O. A. et al. *Asian J Surg* 27:284-290 (2004)), and may have postoperative complications, such as lymphedema, seroma formation, sensory nerve injury, and limitation in range of motion (Purushotham, A. D. et al. *J Clin Oncol* 23:4312-4321 (2005)). The majority of breast cancer patients (74%) who undergo SLN biopsy are pathologically negative (Krag, D. N. et al. *Lancet Oncol* 8:881-888 (2007)). Moreover, biopsies fail to identify axillary disease in 5-10% of patients (McMasters, K. M. et al. *J Clin Oncol* 18:2560-2566 (2000); Ung, O. A. et al. *Asian J Surg* 27:284-290 (2004)). Therefore, a non-invasive method for detecting cancer with improved sensitivity and specificity and eliminating unnecessary surgeries is warranted.

It is an object of the invention to provide compositions and methods for non-invasive detection of cancer in a subject.

It is a particular object of the invention to provide compositions and methods for in vivo molecular imaging of cancer cells, such as metastatic cancer cells, in a subject.

It is a further object of the invention to provide cell-surface markers that can be used to detect cancer cells in vivo.

SUMMARY OF THE INVENTION

A non-invasive method for detecting cancer cells in a subject in vivo has been developed. The method generally involves administering to the subject one or more targeted imaging probes that each specifically binds a cellular target selected from the group consisting of carbonic anhydrase 9 (CAIX), carbonic anhydrase 12 (CAXII), mammaglobin-A, carcinoembryonic antigen-related cell adhesion molecule 6 (CEACAM6), C-X-C motif chemokine 10 (CXCL10), and matrix metallopeptidase 9 (MMP-9). The subject can then be imaged with a molecular imaging device to detect the targeted imaging probe(s) in the subject. With this method, detection of the targeted imaging probe(s) in an organ or tissue of a subject can be an indication of cancer cells in the organ.

The cancer cells can be primary tumors or metastasized cancer cells. Therefore, in some embodiments, the method involves administering targeted imaging probes to a subject diagnosed with a primary tumor to identify metastasized cancer cells. In other embodiments, the method involves administering targeted imaging probes to a subject at risk of cancer to detect primary or occult tumors. Non-limiting examples of cancer cells that can be detected by the disclosed methods include breast cancer cells and non small-cell carcinoma cells.

In preferred embodiments, the cellular target can be CAIX and CAXII. The combination of these cellular targets has been shown to identify 100% of lymph node metastasis from patients with breast cancer. In these embodiments, the method can involve administering to the subject a first targeted imaging probe that specifically binds CAIX and a second targeted imaging probe that specifically binds CAXII, wherein detection of either the first targeted imaging probe or the second targeted imaging probe in an organ of a subject is an indication of cancer cells in the organ.

Mammaglobin-A has also been shown to identify malignant breast cancer cells in breast and lymph nodes. Therefore, in some embodiments, the cellular target is mammaglobin-A. In these embodiments, the method can involve administering to the subject a targeted imaging probe that specifically binds mammaglobin-A, wherein detection of the targeted imaging probe that specifically binds mammaglobin-A in an organ of a subject is an indication of breast cancer cells in the organ.

Devices for use in molecular imaging are known in the art and include, for example, devices for magnetic resonance imaging (MRI), optical imaging, computed tomography (CT), and nuclear medicine imaging. Such devices can be used in the disclosed methods. In preferred embodiments, the molecular imaging device is an optical imaging device that can detect near-infrared light.

In preferred embodiments, the antibodies can be monoclonal antibodies, or fragments thereof that bind the cellular targets. Monoclonal antibodies that specifically bind CAIX, CAXII, mammaglobin-A, CEACAM6, CXCL10, and MMP-9 in vivo are known and commercially available. Moreover, additional antibodies suitable for in vivo detection can be produced using routine methods. In some embodiments, the antibodies or antibody fragments can be chimeric, humanized, human, recombinant, etc.

The targeted imaging probe that specifically binds CAIX preferably contains an antibody having the idiotype of monoclonal antibody clone 303123 linked to a detectable label. The targeted imaging probe that specifically binds CAXII preferably contains an antibody having the idiotype of monoclonal antibody clone 315602 linked to a detectable label. The targeted imaging probe that specifically binds mammaglobin-A preferably contains an antibody having the idiotype of monoclonal antibody clone 304-1A5 or clone 31A5 linked to a detectable label. Therefore, in some embodiments, the targeted imaging probe contains monoclonal antibody clone 303123, clone 315602, clone 304-1A5, or clone 31A5.

The targeted imaging probe is preferably an antibody linked to a detectable label. Suitable detectable labels can be selected based upon the devices used in molecular imaging. In preferred embodiments, the detectable label is a near-infrared (NIR) fluorophore for use with optical imaging. Therefore, the method preferably involves, for example, a first antibody having the idiotype of monoclonal antibody clone 303123 linked to a first NIR fluorophore and a second antibody having the idiotype of monoclonal antibody clone 315602 linked to a second NIR fluorophore.

Also provided is a composition containing a first antibody having the idiotype of monoclonal antibody clone 303123 linked to a first NIR fluorophore and a second antibody having the idiotype of monoclonal antibody clone 315602 linked to a second NIR fluorophore. The composition can further contain a third antibody having the idiotype of monoclonal antibody clone 304-1A5 or clone 31A5 linked to a third NIR fluorophore. Therefore, the composition can contain monoclonal antibody clone 303123, clone 315602, clone 304-1A5, clone 31A5, or any combination thereof. The detectable labels on different targeted imaging probes, for example, can be, the same or different, can have the same, similar, or different excitation and/or emission frequencies, or a combination. For example, different targeted imaging probes that specifically bind different cellular targets can have detectable labels that allow the different targeted imaging probes to be distinguished when imaged, not distinguished when imaged, or a combination (when, for example, three of more targeted imaging probes are used).

A kit is also provided that contains two or more antibodies that specifically bind a cellular target selected from the group consisting of CAIX, CAXII, mammaglobin-A, CEACAM6, CXCL10, and MMP-9 in two or more containers, wherein at least a first antibody is linked to a first NIR fluorophore and at least a second antibody is linked to a second NIR fluorophore. In preferred embodiments, light in either the absorption or emission spectrum of the first NIR fluorophore does not excite the second NIR fluorophore. At least one of the two or more antibodies is preferably monoclonal antibody clone 303123, 315602, or a combination thereof. The kit can also contain monoclonal antibody clone 304-1A5 or clone 31A5.

DETAILED DESCRIPTION OF THE INVENTION

I. Definitions

Figure 1A:
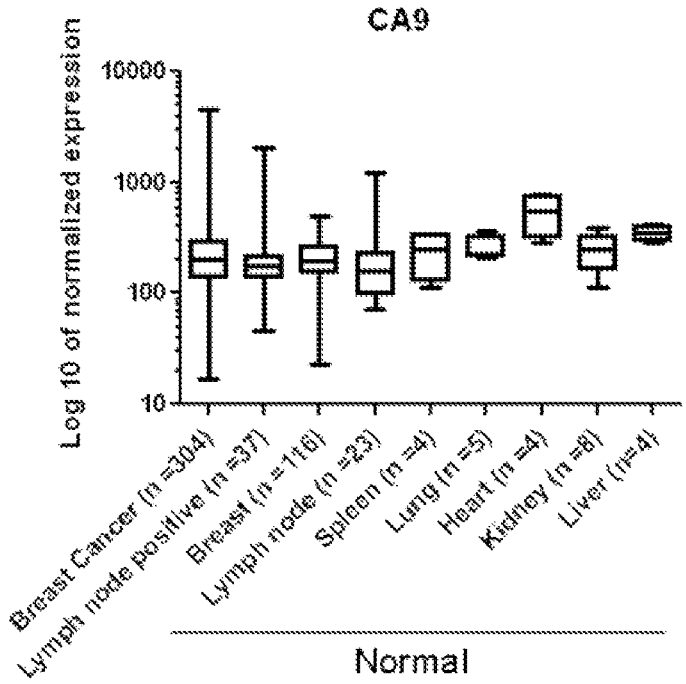
FIGS. 1A and 1B are bar graphs showing CA9 (FIG. 1A) and CA12 (FIG. 1B) mRNA expression ($\log_{10}$ of normalized expression) in breast cancer, lymph node positive, breast, lymph node, spleen, lung, heart, kidney, and liver samples. Data are represented as mean±s.d.
Figure 1B:
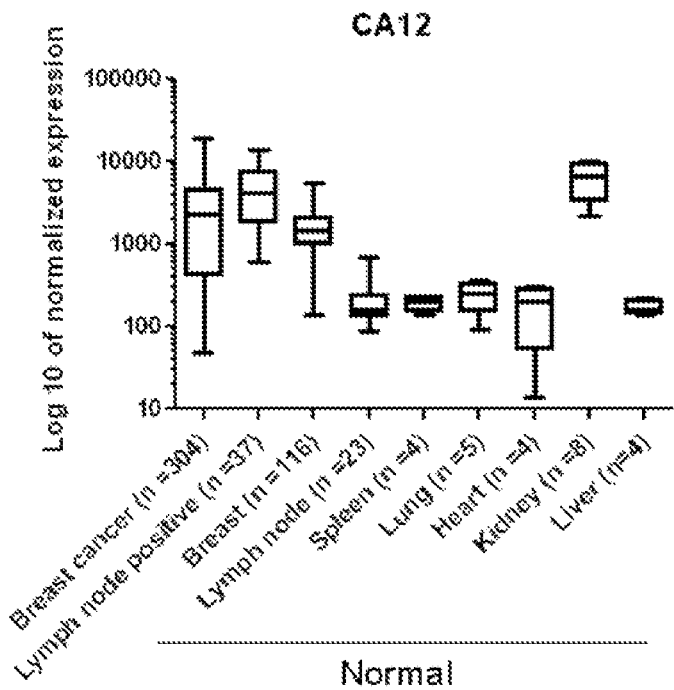

The term "targeted molecular imaging" refers to the in vivo detection of a biological process, such as biodistribution, at the cellular and molecular level. The in vivo detection is accomplished using a targeted imaging probe that specifically binds a molecular or cellular target and an imaging device that detects the probe in vivo.

The term "targeted imaging probe" refers to a molecule that specifically binds to a molecular or cellular target in vivo that can be detected using in vivo imaging techniques. Detection is generally accomplished by linking the binding molecule to a detectable label. Preferred binding molecules include antibodies, peptides, peptidomimetics, and small molecules.

The term "antibody" refers to a polyclonal, monoclonal, recombinant, or synthetic immunoglobulin molecule that specifically binds a target antigen. The term includes intact immunoglobulin molecules, fragments or polymers of those immunoglobulin molecules, chimeric antibodies containing sequences from more than one species, class, or subclass of immunoglobulin, and human or humanized versions of immunoglobulin molecules or fragments thereof containing a least the idiotype of an immunoglobulin that specifically binds the target antigen.

The term "idiotype" refers to the portion of an immunoglobulin molecule that confers the molecule's ability to bind an antigen. The idiotype of an antibody is determined by the complementarity determining regions (CDRs) of the immunoglobulin variable domains ($V_L$ and $V_H$).

The term "peptide" can be used to refer to a natural or synthetic molecule comprising two or more amino acids linked by the carboxyl group of one amino acid to the alpha amino group of another. The peptide is not limited by length; thus "peptide" can include polypeptides and proteins.

The term "peptidomimetic" refers to a mimetic of a peptide which includes some alteration of the normal peptide chemistry. Peptidomimetics typically enhance some property of the original peptide, such as increase stability, increased efficacy, enhanced delivery, increased half life, etc.

The term "aptamer" refers to oligonucleic acid molecules that specifically bind to a target molecule.

As used herein, the term "small molecule" refers to a compound having a molecular weight of less than 1000 Daltons, and typically between 300 and 700 Daltons. The term may include monomers or primary metabolites, secondary metabolites, a biological amine, a steroid, or synthetic or natural, non-peptide biological molecule(s). In the context of targeted imaging probes that are small molecules, the small molecule can specifically bind the molecular or cellular target.

The term "specifically binds" refers to the binding of a molecule to a target molecule, such as an antibody to its cognate antigen, while not significantly binding to other molecules. Preferably, a molecule "specifically binds" to a target molecule with an affinity constant (Ka) greater than about $10^5$ mol$^{-1}$ (e.g., $10^6$ mol$^{-1}$, $10^7$ mol$^{-1}$, $10^8$ mol$^{-1}$, $10^9$ mol$^{-1}$, $10^{10}$ mol$^{-1}$, $10^{11}$ mol$^{-1}$, and $10^{12}$ mol$^{-1}$ or more) with the target molecule.

The term "neoplasm" refers to a cell undergoing abnormal cell proliferation. The growth of neoplastic cells exceeds and is not coordinated with that of the normal tissues around it. The growth typically persists in the same excessive manner even after cessation of the stimuli, and typically causes formation of a tumor. Neoplasms may be benign, premalignant, or malignant.

The term "cancer" or "malignant neoplasm" refers to a cell that displays uncontrolled growth, invasion upon adjacent tissues, and often metastasizes to other locations of the body.

The term "metastatic" or "metastasized" refer to cancer cells that have spread from the site of origin (primary site) to a distant location (metastatic site) in the body.

The term "occult tumor" refers to metastasized cancer cells with unknown primary origin.

The term "subject" or "patient" refers to any individual who is the target of administration. The subject can be a vertebrate, for example, a mammal. Thus, the subject can be a human. The subject can be domesticated, agricultural, or zoo- or circus-maintained animals. Domesticated animals include, for example, dogs, cats, rabbits, ferrets, guinea pigs, hamsters, pigs, monkeys or other primates, and gerbils. Agricultural animals include, for example, horses, mules, donkeys, burros, cattle, cows, pigs, sheep, and alligators. Zoo- or circus-maintained animals include, for example, lions, tigers, bears, camels, giraffes, hippopotamuses, and rhinoceroses. The term does not denote a particular age or sex.

The term "effective amount" refers to an amount of targeted imaging probes sufficient for in vivo detection of the probes in an organ or a tissue by an imaging device. The exact amount required will vary from subject to subject, depending on the age, and general condition of the subject, the organ or tissue that is being imaged, the particular probes used, and its mode of administration. An appropriate "effective amount" can be determined by one of ordinary skill in the art using only routine experimentation.

The term "detectable label" as used herein refers to any molecule that can be detected by in vivo imaging techniques, such as a fluorescent molecule, a metal (e.g., gold), or a radioactive isotope.

The term "near-infrared (NIR) fluorophore" refers to a molecule that has an absorption and emission wavelength in the NIR spectrum between 680 and 900 nm. NIR molecular probes work in a preferential wave range for in vivo fluorescence imaging called "biological window." These molecules can be detected deeper while minimizing the absorption of the fluorescence by tissues.

II. Compositions

A. Targeted Imaging Probes

Targeted imaging probes for detecting cancer cells are provided that specifically bind cellular targets on cancer cells in vivo. In general, the cellular targets can be proteins exposed on the surface of cancer cells and the imaging probes are able to access and bind these targets in vivo. The disclosed targeted imaging probes preferably do not bind normal (non-cancerous) tissue. In some embodiments, the targeted imaging probes bind metastasized cancer cells or cells about to undergo metastasis from the primary tumor.

Probes that specifically bind carbonic anhydrase 9 (CAIX), carbonic anhydrase 12 (CAXII), mammaglobin-A, carcinoembryonic antigen-related cell adhesion molecule 6 (CEACAM6), C-X-C motif chemokine 10 (CXCL10), and matrix metallopeptidase 9 (MMP-9) in vivo are disclosed for use in detecting cancer cells, such as metastasized cancer cells. Targeted imaging probes preferably bind the cellular targets in regions that are accessible from the circulation (e.g., blood or lymph) in vivo.

Targeted imaging probes specifically binding CAIX and CAXII are preferably used together to detect cancer cells expressing either or both of these proteins. These probes can also be used in combination with other tissue specific probes to enhance specificity. For example, CAIX and CAXII probes are preferably used in combination with probes that specifically bind mammaglobin-A to detect metastasized breast cancer cells.

In some embodiments, the disclosed targeted imaging probes are used in combination with other targeting agents, such as other cancer-specific targeting imaging probes. As an example, a targeting agent that specifically binds tumor-associated glycoprotein-72 (TAG-72) is disclosed for use in combination with the disclosed targeted imaging probes. TAG-72 is a glycoprotein found on the surface of many cancer cells, including breast, colon, and pancreatic cells. Murine monoclonal antibody (CC49 MAb, Minretumomab) specifically binds TAG-72 and has strong reactivity with both LS-174T colon cancer extract and to a breast cancer extract.

The targeted imaging probes generally can contain a cellular target binding domain and a detectable label. The cellular target binding domain and detectable label can be linked using routine methods.

In some embodiments, the cellular target binding domain and detectable label can be chemically crosslinked using protein cross-linking agents. Commercially available labels, such as fluorophores generally contain crossing linking agents (such as a succinimidyl ester) for conjugation to proteins, such as antibodies. Non-limiting examples of suitable protein crosslinkers include DSS (Disuccinimidylsuberate), DSP (Dithiobis(succinimidylpropionate)), DTSSP (3,3'-Dithiobis (sulfosuccinimidylpropionate)), SULFO BSOCOES (Bis[2-(sulfosuccinimdooxycarbonyloxy) ethyl] sulfone), BSOCOES (Bis[2-(succinimdooxycarbonyloxy) ethyl]sulfone), SULFO DST (Disulfosuccinimdyltartrate), DST (Disuccinimdyltartrate), SULFO EGS (Ethylene glycolbis(succinimidylsuccinate)), EGS (Ethylene glycolbis (sulfosuccinimidylsuccinate)), DPDPB (1,2-Di[3'-(2'-pyridyldithio) propionamido]butane), BSSS (Bis (sulfosuccinimdyl) suberate), SMPB (Succinimidyl-4-(p-maleimidophenyl) butyrate), SULFO SMPB (Sulfosuccinimdyl-4-(p-maleimidophenyl) butyrate), MBS (3-Maleimidobenzoyl-N-hydroxysuccinimide ester), SULFO MBS (3-Maleimidobenzoyl-N-hydroxysulfosuccinimide ester), SIAB (N-Succinimidyl(4-iodoacetyl) aminobenzoate), SULFO SIAB (N-Sulfosuccinimidyl(4-iodoacetyl) aminobenzoate), SMCC (Succinimidyl-4-(N-maleimidomethyl) cyclohexane-1-carboxylate), SULFO SMCC (Sulfosuccinimidyl-4-(N-maleimidomethyl) cyclohexane-1-carboxylate), NHS LC SPDP (Succinimidyl-6-[3-(2-pyridyldithio) propionamido) hexanoate), SULFO NHS LC SPDP (Sulfosuccinimidyl-6-[3-(2-pyridyldithio) propionamido) hexanoate), SPDP (N-Succinimdyl-3-(2-pyridyldithio) propionate), NHS BROMOACETATE (N-Hydroxysuccinimidylbromoacetate), NHS IODOACETATE (N-Hydroxysuccinimidyliodoacetate), MPBH (4-(N-Maleimidophenyl) butyric acid hydrazide hydrochloride), MCCH (4-(N-Maleimidomethyl) cyclohexane-1-carboxylic acid hydrazide hydrochloride), MBH (m-Maleimidobenzoic acid hydrazidehydrochloride), SULFO EMCS (N-(epsilon-Maleimidocaproyloxy) sulfosuccinimide), EMCS (N-(epsilon-Maleimidocaproyloxy) succinimide), PMPI (N-(p-Maleimidophenyl) isocyanate), KMUH (N-(kappa-Maleimidoundecanoic acid) hydrazide), LC SMCC (Succinimidyl-4-(N-maleimidomethyl)-cyclohexane-1-carboxy(6-amidocaproate)), SULFO GMBS (N-(gamma-Maleimidobutryloxy) sulfosuccinimide ester), SMPH (Succinimidyl-6-(beta-maleimidopropionamidohexanoate)), SULFO KMUS (N-(kappa-Maleimidoundecanoyloxy)sulfosuccinimide ester), GMBS (N-(gamma-Maleimidobutyrloxy) succinimide), DMP (Dimethylpimelimidate hydrochloride), DMS (Dimethylsuberimidate hydrochloride), MHBH (Wood's Reagent) (Methyl-p-hydroxybenzimidate hydrochloride, 98%), and DMA (Dimethyladipimidate hydrochloride).

In other embodiments, the targeted imaging probe can be a fusion peptide or protein containing the cellular target binding domain and a detectable label. Fusion are proteins created through the joining of two or more genes or coding regions that originally coded (and/or were designed to code for) for separate peptides or proteins. Translation of this fusion gene or coding region results in a single peptide or polypeptide with functional properties derived from each of the original peptide or proteins. Recombinant fusion peptide or proteins can be created artificially by recombinant DNA technology. This typically involves removing the stop codon from a cDNA sequence coding for the first peptide or protein, then appending the cDNA sequence of the second peptide or protein in frame through ligation or overlap extension PCR. Alternatively, the coding regions can be synthesized and then joined or can even be synthesized as a fusion coding region. The resulting fusion DNA sequence can then be expressed by a cell as a single peptide or protein.

The protein can be engineered to include the full sequence of both original peptides or proteins, or only a portion of either. If the two entities are proteins, often linker (or "spacer") peptides can also be added that make it more likely that the proteins fold independently and behave as expected. Alternatively, internal ribosome entry sites (IRES) elements can be used to create multigene, or polycistronic, messages. IRES elements are able to bypass the ribosome scanning model of 5' methylated Cap dependent translation and begin translation at internal sites. Multiple open reading frames can be transcribed together, each separated by an IRES, creating polycistronic messages. By virtue of the IRES element, each open reading frame is accessible to ribosomes for efficient translation. IRES sequences are known in the art and include those from encephalomycarditis virus (EMCV) (Ghattas, I. R. et al., Mol. Cell. Biol., 11:5848-5849 (1991); BiP protein (Macejak and Sarnow, Nature, 353:91 (1991)); the Antennapedia gene of drosophilia (exons d and e) [Oh et al., Genes & Development, 6:1643-1653 (1992)); those in polio virus [Pelletier and Sonenberg, Nature, 334:320325 (1988); see also Mountford and Smith, TIG, 11:179-184 (1985)). Numerous other recombinant and fusion techniques are known and can be adapted for producing the disclosed peptides and proteins.

1. Cellular Target Binding Domain a. Antibodies

In preferred embodiments, the targeted imaging probes are antibodies that specifically bind the cellular targets. Therefore, antibodies that specifically bind CAIX, CAXII, mammaglobin-A, CEACAM6, CXCL10, and MMP-9 are disclosed for use in the disclosed compositions and methods.

The anti-CAIX antibody preferably specifically binds human CAIX protein (Accession No. NP_001207). In some embodiments, the anti-CAIX antibody specifically binds the N-terminus and the extracellular domain of human CAIX. In particularly preferred embodiments, the anti-CAIX antibody specifically binds amino acids 59-414 of human CAIX protein. As an example, the anti-CAIX antibody can be the monoclonal antibody (mAb) clone 303123 (R&D systems) or can have the idiotype of this clone. In addition, suitable anti-CAIX antibody can be identified that bind the same epitope as this clone.

The anti-CAXII antibody preferably specifically binds human CAXII protein (Accession No. NP_001209). In some embodiments, the anti-CAXII antibody specifically binds the N-terminus and the extracellular domain of human CAXII. In particularly preferred embodiments, the anti-CAXII antibody specifically binds amino acids 25- 291 of human CAXII protein. As an example, the anti-CAXII antibody can be the monoclonal antibody (mAb) clone 315602 (R&D systems) or can have the idiotype of this clone. In addition, suitable anti-CAXII antibody can be identified that bind the same epitope as this clone.

The anti-Mammaglobin-A antibody preferably specifically binds human Mammaglobin-A (Accession No. NP_002402.1). As an example, the anti-Mammaglobin-A antibody can be the monoclonal antibody (mAb) clone 304-1A5 or 31A5 (Zeta Corp., Calif., Sierra Madre) or can have the idiotype of one of these clones. In addition, suitable anti-Mammaglobin-A antibody can be identified that bind the same epitope as this clone.

Antibodies that can be used in the disclosed compositions and methods include whole immunoglobulin (i.e., an intact antibody) of any class, fragments thereof, and synthetic proteins containing at least the antigen binding variable domain of an antibody. The variable domains differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a beta-sheet configuration, connected by three CDRs, which form loops connecting, and in some cases forming part of, the beta-sheet structure. The CDRs in each chain are held together in close proximity by the FR regions and, with the CDRs from the other chain, contribute to the formation of the antigen binding site of antibodies.

Antibodies for use in the disclosed compositions and methods can be of any isotype, including IgG, IgA, IgE, IgD, and IgM. IgG isotype antibodies can be further subdivided into IgG1, IgG2, IgG3, and IgG4 subtypes. IgA antibodies can be further subdivided into IgA1 and IgA2 subtypes.

Also disclosed are fragments of antibodies which have bioactivity. The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. Fab is the fragment of an antibody that contains a monovalent antigen-binding fragment of an antibody molecule. A Fab fragment can be produced by digestion of whole antibody with the enzyme papain to yield an intact light chain and a portion of one heavy chain. Fab' is the fragment of an antibody molecule can be obtained by treating whole antibody with pepsin, followed by reduction, to yield an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region. (Fab')$_2$ is the fragment of an antibody that can be obtained by treating whole antibody with the enzyme pepsin without subsequent reduction. F(ab')$_2$ is a dimer of two Fab' fragments held together by two disulfide bonds. Fv is the minimum antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

Techniques can also be adapted for the production of single-chain antibodies specific for the cellular targets. Single chain antibody ("SCA"), defined as a genetically engineered molecule containing the variable region of the light chain ($V_L$), the variable region of the heavy chain ($V_H$), linked by a suitable polypeptide linker as a genetically fused single chain molecule. Such single chain antibodies are also referred to as "single-chain Fv" or "sFv" antibody fragments. Generally, the Fv polypeptide further comprises a polypeptide linker between the $V_H$ and $V_L$ domains that enables the sFv to form the desired structure for antigen binding. Methods for the production of single-chain antibodies are well known to those of skill in the art. A single chain antibody can be created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding. The linker is chosen to permit the heavy chain and light chain to bind together in their proper conformational orientation.

Divalent single-chain variable fragments (di-scFvs) can be engineered by linking two scFvs. This can be done by producing a single peptide chain with two $V_H$ and two $V_L$ regions, yielding tandem scFvs. ScFvs can also be designed with linker peptides that are too short for the two variable regions to fold together (about five amino acids), forcing scFvs to dimerize. This type is known as diabodies. Diabodies have been shown to have dissociation constants up to 40-fold lower than corresponding scFvs, meaning that they have a much higher affinity to their target. Still shorter linkers (one or two amino acids) lead to the formation of trimers (triabodies or tribodies). Tetrabodies have also been produced. They exhibit an even higher affinity to their targets than diabodies.

Preferably, if the antibody is to be administered to humans, the antibody is a human antibody or is a "humanized" antibody derived from a non-human animal. Methods for humanizing non-human antibodies are known in the art and have been described in, for example, U.S. Pat. Nos. 5,530,101; 5,585,089; 5,693,762; 6,180,370; and 6,407,213.

b. Peptides

In some embodiments, the targeted imaging probe can contain a peptide that binds the cellular target CAIX, CAXII, mammaglobin-A, CEACAM6, CXCL10, or MMP-9. In some embodiments, the peptide comprises the idiotype of an antibody, such as those described above. In other embodiments, the peptide can be identified by screening a library of peptides against the cellular target.

c. Peptidomimetics

In some embodiments, the targeted imaging probe can contain a peptidomimetic that binds CAIX, CAXII, mammaglobin-A, CEACAM6, CXCL10, or MMP-9. A peptidomimetic is a small protein-like chain designed to mimic a peptide. They typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. This can have a role in the development of drug-like compounds from existing peptides. These modifications involve changes to the peptide that will not occur naturally (such as altered backbones and the incorporation of nonnatural amino acids).

Methods of making peptidomimetics based upon a known polypeptide sequence is described, for example, in U.S. Pat. Nos. 5,631,280; 5,612,895; and 5,579,250. Peptidomimetics can have a non-amino acid residue with non-amide linkages at a given position. Some non-limiting examples of unnatural amino acids which may be suitable amino acid mimics include β-alanine, L-α-amino butyric acid, L-γ-amino butyric acid, L-α-amino isobutyric acid, L-α-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZ-L-ornithine, Boc-p-nitro-L-phenylalanine, Boc-hydroxyproline, and Boc-L-thioproline.

d. Aptamers

In some embodiments, the targeted imaging probe can contain an aptamer that binds CAIX, CAXII, mammaglobin-A, CEACAM6, CXCL10, or MMP-9. Aptamers are single-stranded RNA or DNA oligonucleotides 15 to 60 base in length that bind with high affinity to specific molecular targets. Most aptamers to proteins bind with Kds (equilibrium constant) in the range of 1 pM to 1 nM, similar to monoclonal antibodies. These nucleic acid ligands bind to nucleic acid, proteins, small organic compounds, and even entire organisms.

Aptamers can be selected by incubating the target molecule in a large (e.g., 1010 to 1020) pool of oligonucleotide (usually 40 to 60mers). The large pool size of the oligonucleotide ensures the selection and isolation of the specific aptamer. Aptamers can distinguish between closely related but non-identical members of a protein family, or between different functional or conformational states of the same protein. The protocol called systematic evolution of ligands by exponential enrichment (SELEX) is generally used with modification and variations for the selection of specific aptamers. Using this process, it is possible to develop new aptamers in as little as two weeks.

e. Sulfonamide-Based Inhibitors

In some embodiments, the targeted imaging probe can contain a carbonic anhydrase inhibitor that binds CAIX and/or CAXII. Carbonic anhydrase inhibitors are a class of pharmaceuticals that suppress the activity of carbonic anhydrase by binding to its catalytic site. Suitable carbonic anhydrase inhibitors generally contain a sulfonamide group. Non-limiting examples of carbonic anhydrase inhibitors include Acetazolamide, Brinzolamide, Methazolamide, Dorzolamide, and Topiramate.

2. Detectable Labels

The disclosed targeted imaging probes are preferably linked to a detectable label. Substances suitable for detectably labeling imaging agents include fluorescent molecules (a.k.a. fluorochromes and fluorophores), chemiluminescent reagents (e.g., luminol), bioluminescent reagents (e.g., luciferin and green fluorescent protein (GFP)), metals (e.g., gold nanoparticles), and radioactive isotopes (radioisotopes). Suitable detectable labels can be selected based on the choice of imaging method. For example, in preferred embodiments, the detectable label is near infrared fluorescent dye for optical imaging, a Gadolinium chelate for MRI imaging, a radionuclide for PET or SPECT imaging, or a gold nanoparticle for CT imaging.

a. Fluorophores

Fluorophores are compounds or molecules that absorb energy of a specific wavelength and re-emit energy at a different (but equally specific) wavelength. In preferred embodiments, the detectable label is a near-infrared (NIR) fluorophore. Suitable NIRs include, but are not limited to, VivoTag-S® 680 and 750, Kodak X-SIGHT Dyes and Conjugates, DyLight 750 and 800 Fluors, Cy 5.5 and 7 Fluors, Alexa Fluor 680 and 750 Dyes, and IRDye 680 and 800CW Fluors. In some embodiments, Quantum dots, with their photostability and bright emissions, can also be used with optical imaging.

b. Radioisotopes

A radioisotope can be incorporated into or attached directly to a targeted imaging agent. Examples of useful radioisotopes include, but are not limited to, tritium, $^{11}C$, $^{13}$N, $^{14}$C, $^{15}$O, $^{18}$Fl, $^{62}$Cu, $^{64}$Cu, $^{67}$Cu, $^{68}$Ga, $^{76}$Br, $^{82}$Rb, $^{90}$Y, $^{99m}$Tc, $^{111}$In, $^{123}$I, $^{124}$I, $^{125}$I, $^{131}$I, $^{153}$Sm, $^{201}$Tl, $^{186}$Re, $^{188}$Re, and $^{212}$Bi. In some embodiments, the radioisotope is attached to the targeted imaging agent by halogenation. In some embodiments, the radioisotopes is attached to the targeted imaging agent by a linking group or bound by a chelating group, which is then attached to the targeted imaging agent directly or by means of a linker.

B. Pharmaceutical Formulations

Pharmaceutical formulations are provided that contain one or more targeted imaging probes in combination with one or more pharmaceutically acceptable excipients.

1. Pharmaceutically Acceptable Excipients

The disclosed targeted imaging probes are preferably formulated for parenteral administration. Parenteral formulations can be prepared as aqueous compositions using techniques is known in the art. Typically, such compositions are prepared as solutions or suspensions; solid forms suitable to prepare solutions or suspensions upon the addition of a reconstitution medium; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof.

Solutions and dispersions of the active compounds as the free acid or base or pharmacologically acceptable salts thereof can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation may also contain an antioxidant to prevent degradation of the active agent(s).

The formulation is typically buffered to a pH of 3-8 for parenteral administration upon reconstitution. Suitable buffers include, but are not limited to, phosphate buffers, acetate buffers, and citrate buffers.

Water soluble polymers are often used in formulations for parenteral administration. Suitable water-soluble polymers include, but are not limited to, polyvinylpyrrolidone, dextran, carboxymethylcellulose, and polyethylene glycol.

Sterile injectable solutions can be prepared by incorporating the active compounds in the required amount in the appropriate solvent or dispersion medium with one or more of the excipients listed above, as required, followed by filtered sterilization. Generally, dispersions are prepared by incorporating the various sterilized active ingredients into a sterile vehicle which contains the basic dispersion medium and the required other ingredients from those listed above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. The powders can be prepared in such a manner that the particles are porous in nature, which can increase dissolution of the particles. Methods for making porous particles are well known in the art.

2. Dosage

Targeted imaging probes are preferably administered in a dose equivalent to parenteral administration of about 0.1 ng to about 100 g per kg of body weight, such as about 10 ng to about 50 g per kg of body weight, about 100 ng to about 1 g per kg of body weight, from about 1 μg to about 100 mg per kg of body weight, from about 1 μg to about 50 mg per kg of body weight, from about 1 mg to about 500 mg per kg of body weight, and from about 1 mg to about 50 mg per kg of body weight. For example, the amount of targeted imaging probes administered to achieve an effective dose for imaging can be about 0.1 ng, 1 ng, 10 ng, 100 ng, 1 μg, 10 μg, 100 μg, 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 30 mg, 40 mg, 50 mg, 60 mg, 70 mg, 80 mg, 90 mg, 100 mg, 500 mg per kg of body weight or greater.

C. Kits

One or more of the compositions described herein can be assembled in kits. Printed instructions, either as inserts or as labels, indicating quantities of the components to be administered, guidelines for administration, and/or guidelines for mixing the components, can also be included in the kit. Kits of the invention can optionally include pharmaceutically acceptable carriers and/or diluents.

The disclosed kit can contain, for example, antibodies that specifically bind one, two, three, or more of CAIX, CAXII, mammaglobin-A, CEACAM6, CXCL10, and MMP-9. In preferred embodiments, the disclosed kit can contain antibodies that specifically bind CAIX and CAXII. In some embodiments, the disclosed kit can contain antibodies that specifically bind CAIX, CAXII, and mammaglobin-A. In these embodiments, the antibodies that specifically bind different cellular targets can in some embodiments be linked to the same detectable label, or to a different label that is indistinguishable by the imaging device. In preferred embodiments, the antibodies that specifically bind different cellular targets can be linked to different detectable labels that are distinguishable by the imaging device. For example, where the detectable label is a near-infrared (NIR) fluorophore, the NIR fluorphores preferably absorb and emit at different wavelengths.

In preferred embodiments a pharmaceutical composition can be provided in the kit as a liquid or solution. The kit can also include means of administration, such as one or more of a syringe (e.g., a barrel syringe or a bulb syringe), intravenous (IV) bag, IV line, IV needle, and/or cannula. In some embodiments, the kit can comprise an ampoule or syringe containing a pharmaceutical compositions in liquid or solution form Kits can include one or more containers containing a one or more targeted imaging probes disclosed herein. Containers of the kit can be of any suitable material, e.g., glass, plastic, metal, etc., and of any suitable size, shape, or configuration.

III. Methods

A. Detecting Cancer In Vivo

The disclosed targeted imaging probes can be used in combination with molecular imaging to detect cancer cells, such as those that have metastasized and therefore spread to another organ or tissue of the body, using an in vivo imaging device. A non-invasive method is therefore provided for detecting cancer cells in a subject that involves administering a pharmaceutical composition containing targeted imaging probes to the subject and then detecting the biodistribution of the targeted imaging probes using an imaging device. In some embodiments, the pharmaceutical composition is injected into the parenchyma. In other embodiments, the pharmaceutical composition is injected into the circulation.

The disclosed targeted imaging probes can also be used for intraoperative detection of cancer cells. For example, the disclosed targeted imaging probes can be used for intraoperative lymphatic mapping (ILM) to trace the lymphatic drainage patterns in a cancer patient to evaluate potential tumor drainage and cancer spread in lymphatic tissue. In these embodiments, the targeted imaging probes are injected into the tumor and their movement through the lymphatic system is traced using a molecular imaging device. As another example, the disclosed targeted imaging probes can be used for intraoperative assessment of, for example, tumor margins and tumor proximal tissues for the presence of cancer cells. This can be useful, for example, in effectively resecting tumors and detecting the spread of cancer proximal to the tumor.

The disclosed methods of imaging to detect cancer cells are referred to herein as non-invasive. By non-invasive is meant that the targeted imaging probes can be detected from outside of the subject's body. By this it is generally meant that the signal detection device is located outside of the subject's body. It is understood, however, that the disclosed targeted imaging probes can also be detected from inside the subject's body or from inside the subject's gastrointestinal tract or from inside the subject's respiratory system and that such methods of imaging are also specifically contimplated. For example, for intraoperative detection, the signal detection device can be located either outside or inside of the subject's body. From this it should be understood that the a non-invasive method of imaging can be used along with, at the same time as, or in combination with an invasive procedure, such as surgery.

In some embodiments, the method can be used to diagnose cancer in a subject or detect cancer in a particular organ of a subject. A particularly useful aspect of this method is the ability to search for metastatic cancer cells in secondary tissues or organs, such as lymph nodes, or at or near tumor margins. Therefore, the disclosed methods can be used for assessing lymph node status in patients that have or are suspected of having cancer, such as breast cancer. This avoids the need to biopsy the tissue or organ, e.g., remove a lymph node. In some embodiments, the method involves administering to the patient targeted imaging probes and detecting whether the probes have bound to cells in a lymph node. In some of these embodiments, the lymph node can be an axillary lymph node (ALN). In other embodiments, the lymph node can be a sentinel lymph node. In further embodiments, both axillary and sentinel lymph nodes can be assessed for binding of the agent to cells in the lymph node.

The method can also be used with other therapeutic or diagnostic methods. For example, the method can also be used during an operation to, for example, guide cancer removal, which is referred to herein as "intraoperative guidance" or "image guided surgery." In a particular embodiment, the method can be used for therapeutic treatment to remove or destroy cancer cells in a patient's lymph nodes. For example, targeted imaging probes can be administered to a patient, and the location of cancerous tissue (e.g., lymph nodes) can be determined and removed using image guided surgery. In another preferred embodiment, the method can be used for therapeutic treatment to prevent positive microscopic margins after tumor resection. For example, targeted imaging probes can be administered to a patient, the location of cancer cells around a tumor can be determined, and the complete tumor removed using image guided surgery. In these embodiments, the physician administers targeted imaging probes to the patient and uses an imaging device to detect the cancer cells, guide resection of tissue, and assure that all of the cancer is removed, i.e., negative cancer margins. In addition, the imaging device can be used post-operatively to determine if any cancer remains or reoccurs.

In some embodiments, the targeted imaging probes can be linked to a therapeutic compound. The therapeutic compound or moiety can be one that kills or inhibits cancer cells directly (e.g., cisplatin) or it can be one that can kill or inhibit a cancer cell indirectly (e.g., gold nanoparticles that kill or destroy cancer cells when heated using a light source). If the therapeutic compound or moiety is one that kills or inhibits a cancer cell indirectly, then the method further comprises a step of taking appropriate action to "activate" or otherwise implement the anti-cancer activity of the compound or moiety. In a specific embodiment, the therapeutic compound or moiety attached to the agent can be a gold nanoparticle and following administration to the patient and binding of the agent to cancer cells, the gold nanoparticles are heated, e.g., using a laser light, to kill or destroy the nearby cancer cells (photothermal ablation). For example, in some embodiments, the method involves image guided surgery using targeted imaging probes to detect and resect cancer from a subject followed by the use of the same or different targeted imaging probes linked to a therapeutic compound to kill remaining cancer cells.

1. Cancers

In some embodiments, the cancer of the disclosed methods can be any cell in a subject undergoing unregulated growth. In preferred embodiments, the cancer is any cancer cell capable of metastasis. For example, the cancer can be a sarcoma, lymphoma, leukemia, carcinoma, blastoma, or germ cell tumor. A representative but non-limiting list of cancers that the disclosed compositions can be used to detect include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

In preferred embodiments, the cancer is breast cancer. Breast cancers originating from ducts are known as ductal carcinomas, and those originating from lobules that supply the ducts with milk are known as lobular carcinomas. Common sites of breast cancer metastasis include bone, liver, lung and brain.

In other preferred embodiments, the cancer is non-small-cell lung carcinoma (NSCLC). NSCLC is any type of epithelial lung cancer other than small cell lung carcinoma (SCLC). The most common types of NSCLC are squamous cell carcinoma, large cell carcinoma, and adenocarcinoma, but there are several other types that occur less frequently, and all types can occur in unusual histologic variants and as mixed cell-type combinations.

2. Molecular Imaging

Methods are disclosed for in vivo detection of cancer cells using the disclosed targeted imaging probes in combination with a molecular imaging device. Molecular imaging differs from traditional imaging in that probes known as biomarkers are used to help image particular targets or pathways. There are many different modalities that can be used for noninvasive molecular imaging. Each have their different strengths and weaknesses and some are more adept at imaging multiple targets than others.

a. Magnetic Resonance Imaging (MRI)

MRI has the advantages of having very high spatial resolution and is very adept at morphological imaging and functional imaging. However, MRI has a sensitivity of around $10^{-3}$ mol/L to $10^{-5}$ mol/L which, compared to other types of imaging, can be very limiting. This problem stems from the fact that the difference between atoms in the high energy state and the low energy state is very small. For example, at 1.5 tesla, a typical field strength for clinical MRI, the difference between high and low energy states is approximately 9 molecules per 2 million. Improvements to increase MR sensitivity include hyperpolarization by increasing magnetic field strength, optical pumping, or dynamic nuclear polarization. There are also a variety of signal amplification schemes based on chemical exchange that increase sensitivity.

b. Optical Imaging

There are a number of approaches used for optical imaging. The various methods depend upon fluorescence, bioluminescence, absorption or reflectance as the source of contrast. Optical imaging's most valuable attribute is that it does not have strong safety concerns like the other medical imaging modalities. The downside of optical imaging is the lack of penetration depth, especially when working at visible wavelengths. Depth of penetration is related to the absorption and scattering of light, which is primarily a function of the wavelength of the excitation source. Light is absorbed by endogenous chromophores found in living tissue (e.g. hemoglobin, melanin, and lipids). In general, light absorption and scattering decreases with increasing wavelength. Below ~700 nm (e.g. visible wavelengths), these effects result in shallow penetration depths of only a few millimeters. Thus, in the visible region of the spectrum, only superficial assessment of tissue features is possible. Above 900 nm, water absorption can interfere with signal-to-background ratio. Because the absorption coefficient of tissue is considerably lower in the near infrared (NIR) region (680-900 nm), light can penetrate more deeply, to depths of several centimeters.

Fluorescent probes and labels are an important tool for optical imaging. A number of near-infrared (NIR) fluorophores have been employed for in vivo imaging, including Kodak X-SIGHT Dyes and Conjugates, DyLight 750 and 800 Fluors, Cy 5.5 and 7 Fluors, Alexa Fluor 680 and 750 Dyes, IRDye 680 and 800CW Fluors. In some embodiments, the detectable label is a Quantum dot.

c. Nuclear Medicine Imaging

Nuclear medicine imaging involves the use and detection of radioisotopes in the body. Nuclear medicine imaging techniques include scintigraphy, single photon emission computed tomography (SPECT), and positron emission tomography (PET). In these techniques, radiation from the radioisotopes is captured by a gamma camera to form two-dimensional images (scintigraphy) or 3-dimensional images (SPECT and PET).

Suitable gamma-emitting radioisotopes for scintigraphy and SPECT include $^{99m}$Tc, $^{111}$In, $^{123}$I, $^{133}$Xe, $^{201}$Tl. Suitable radioisotopes have relatively long half lives (a few hours to a few days) making them easy to produce and relatively cheap. This represents a major advantage, since it is significantly cheaper than either PET or MRI. However it lacks good spatial resolution. Additionally, due to the radioactivity of the contrast agent, there are safety aspects concerning the administration of radioisotopes to the subject, especially for serial studies.

Radionuclides used in PET scanning are typically isotopes with short half-lives. Typical isotopes include $^{11}$C, $^{13}$N, $^{15}$O, $^{18}$F, $^{64}$Cu, $^{62}$Cu, $^{124}$I, $^{76}$Br, $^{82}$Rb and $^{68}$Ga, with $^{18}$F being the most clinically utilized. One of the major disadvantages of PET is that most of the probes must be made with a cyclotron. Most of these probes also have a half life measured in hours, forcing the cyclotron to be on site. PET imaging is, however, very sensitive. A typical PET scanner can detect between $10^{-11}$ mol/L to $10^{-12}$ mol/L concentrations.

Gamma radiation from radioisotopes is detected using a gamma particle detection device. In some embodiments, the gamma particle detection device is a Gamma Finder® device (SenoRx, Irvine Calif.). In some embodiments, the gamma particle detection device is a neoprobe® GDS gamma detection system (Dublin, Ohio).

B. Administration

The disclosed pharmaceutical compositions are preferably administered parenterally into the parenchyma or into the circulation so that the targeted imaging probes reach target tissues where cancer cells may be located. In some preferred embodiments, the pharmaceutical composition is administered directly into or adjacent to a tumor mass. In other preferred embodiments, the pharmaceutical composition is administered intravenously. In still other embodiments, the pharmaceutical composition is administered intraperitoneally, intramuscularly, subcutaneously, intracavity, or transdermally.

Parenteral administration of the composition, if used, is generally characterized by injection. Injectables can be prepared in conventional forms, either as liquid solutions or suspensions, solid forms suitable for solution of suspension in liquid prior to injection, or as emulsions. A revised approach for parenteral administration involves use of a slow release or sustained release system such that a constant dosage is maintained.

C. Actions Based on Imaging and Identifications

The disclosed methods include the determination, identification, indication, correlation, diagnosis, prognosis, etc. (which can be referred to collectively as "identifications") of subjects, diseases, conditions, states, etc. based on imagings, measurements, detections, comparisons, analyses, assays, screenings, etc. For example, the disclosed imaging methods allow identification of patients, organs, tissues, etc. having cancer cells, metastasized cancer cells, cancer cells beyond tumor margins, etc. Such identifications are useful for many reasons. For example, and in particular, such identifications allow specific actions to be taken based on, and relevant to, the particular identification made. For example, diagnosis of a particular disease or condition in particular subjects (and the lack of diagnosis of that disease or condition in other subjects) has the very useful effect of identifying subjects that would benefit from treatment, actions, behaviors, etc. based on the diagnosis. For example, treatment for a particular disease or condition in subjects identified is significantly different from treatment of all subjects without making such an identification (or without regard to the identification). Subjects needing or that could benefit from the treatment will receive it and subjects that do not need or would not benefit from the treatment will not receive it.

Accordingly, also disclosed herein are methods comprising taking particular actions following and based on the disclosed identifications. For example, disclosed are methods comprising creating a record of an identification (in physical—such as paper, electronic, or other—form, for example). Thus, for example, creating a record of an identification based on the disclosed methods differs physically and tangibly from merely performing a imaging, measurement, detection, comparison, analysis, assay, screen, etc. Such a record is particularly substantial and significant in that it allows the identification to be fixed in a tangible form that can be, for example, communicated to others (such as those who could treat, monitor, follow-up, advise, etc. the subject based on the identification); retained for later use or review; used as data to assess sets of subjects, treatment efficacy, accuracy of identifications based on different imagings, measurements, detections, comparisons, analyses, assays, screenings, etc., and the like. For example, such uses of records of identifications can be made, for example, by the same individual or entity as, by a different individual or entity than, or a combination of the same individual or entity as and a different individual or entity than, the individual or entity that made the record of the identification. The disclosed methods of creating a record can be combined with any one or more other methods disclosed herein, and in particular, with any one or more steps of the disclosed methods of identification.

As another example, disclosed are methods comprising making one or more further identifications based on one or more other identifications. For example, particular treatments, monitorings, follow-ups, advice, etc. can be identified based on the other identification. For example, identification of a subject as having a disease or condition with a high level of a particular component or characteristic can be further identified as a subject that could or should be treated with a therapy based on or directed to the high level component or characteristic. A record of such further identifications can be created (as described above, for example) and can be used in any suitable way. Such further identifications can be based, for example, directly on the other identifications, a record of such other identifications, or a combination. Such further identifications can be made, for example, by the same individual or entity as, by a different individual or entity than, or a combination of the same individual or entity as and a different individual or entity than, the individual or entity that made the other identifications. The disclosed methods of making a further identification can be combined with any one or more other methods disclosed herein, and in particular, with any one or more steps of the disclosed methods of identification.

As another example, disclosed are methods comprising treating, monitoring, following-up with, advising, etc. a subject identified in any of the disclosed methods. Also disclosed are methods comprising treating, monitoring, following-up with, advising, etc. a subject for which a record of an identification from any of the disclosed methods has been made. For example, particular treatments, monitorings, follow-ups, advice, etc. can be used based on an identification and/or based on a record of an identification. For example, a subject identified as having a disease or condition with a high level of a particular component or characteristic (and/or a subject for which a record has been made of such an identification) can be treated with a therapy based on or directed to the high level component or characteristic. Such treatments, monitorings, follow-ups, advice, etc. can be based, for example, directly on identifications, a record of such identifications, or a combination. Such treatments, monitorings, follow-ups, advice, etc. can be performed, for example, by the same individual or entity as, by a different individual or entity than, or a combination of the same individual or entity as and a different individual or entity than, the individual or entity that made the identifications and/or record of the identifications. The disclosed methods of treating, monitoring, following-up with, advising, etc. can be combined with any one or more other methods disclosed herein, and in particular, with any one or more steps of the disclosed methods of identification.

The disclosed imagings, measurements, detections, comparisons, analyses, assays, screenings, etc. can be used in other ways and for other purposes than those disclosed. For example, imaging of cancer cells can be used to identify areas of organs of tissues or margins of cancer-affected organs or tissues. Thus, the disclosed imagings, measurements, detections, comparisons, analyses, assays, screenings, etc. do not encompass all uses of such imagings, measurements, detections, comparisons, analyses, assays, screenings, etc.

EXAMPLES

Example 1

Microarray and TMA Studies on Patient Tissue Samples

Materials and Methods

DNA microarray analysis: A list of 3,800 cell surface genes was compiled from Gene Bank and used to filter Affymetrix® expression microarray data from 304 breast cancer samples of which 37 were noted as being from LN positive patients; and from normal tissues including 116 normal breast, 23 lymph node, 4 spleen, 5 lung, 4 heart, 8 kidney and 4 liver samples. The Affymetrix® CEL files for the tumor samples were downloaded from the Gene Expression Omnibus (GEO) database ([[www.]] ncbi.nlm.nih.gov/projects/geo/index.cgi), data series GSE2109. This is the Expression Project for Oncology carried out by the International Genomics Consortium (IGC). Normal tissue data were from the GEO data series GSE7307, Human Body Index, which was a transcriptional profiling project carried out by Neurocrine Biosciences, Inc. The CEL files were analyzed using the MAS 5.0 algorithm (Affymetrix Corp.) and then screened through a rigorous quality control panel to remove samples with low percentages of probe sets called present by the MAS 5 algorithm, indicating problems with the amplification process; high scaling factors, indicating poor transcript abundance during hybridization; and poor 3'/5' ratios, indicating RNA degradation either prior to or during processing. The remaining samples were normalized to the trimmed average of 500 in the MAS 5 algorithm.

Immunohistochemistry (IHC) of tissue mircroarray (TMA): A TMA was constructed at the Tissue Core of Moffitt Cancer Center containing human breast tissue samples of formalin-fixed and paraffin-embedded (FFPE) specimens. The TMA contains 50 normal breast tissue, 50 ductal carcinoma in situ, 50 invasive ductal carcinomas without metastasis, 50 invasive ductal carcinomas with metastasis, and 50 lymph node with macrometastases of breast. The procedure of the TMA construction and the protocol were described previously (Schlauder, S. M. et al. Fetal Pediatr Pathol 27:83-97 (2008)). For the current project, a 1:500 dillution of anti-CAXII antibody (Prestige Antibodies Powered by Atlas Antibodies, Sigma-Aldrich) was used as a primary antibody for CAXII staining and a 1:500 dillution of anti-CAIX rabbit polyclonal antibody (Abcam plc) was used for CAIX staining.

Statistics: Data are represented as mean±s.d. and Student's t-test was used to determine significance.

Results

CAIX and CAXII were identified and validated as cell-surface markers for breast cancer lymph node (LN) metastasis. CAIX expression is observed in a variety of cancer types including breast cancer (Brennan, D. J. et al. Clin Cancer Res 12:6421-6431 (2006); Chia, S. K. et al. J Clin Oncol 19:3660-3668 (2001); Colpaert, C. G. et al. Breast Cancer Res Treat 81:137-147 (2003); Hussain, S. A. et al. Br J Cancer 96:104-109 (2007); Lancashire, L. J. et al. Breast Cancer Res Treat 120:83-93 (2010); Span, P. N. et al. Br J Cancer 89:271-276 (2003); Trastour, C. et al. Int J Cancer 120:1451-1458 (2007)), but is relatively absent from corresponding normal tissues (Supuran, C. T. et al. ioorg Med Chem 15:4336-4350 (2007)). CAIX expression is correlated with high tumor grade and increased tumor size in breast cancer (Chia, S. K. et al. J Clin Oncol 19:3660-3668 (2001); Span, P. N. et al. Br J Cancer 89:271-276 (2003)).

To identify additional targets, a list of 3800 cell surface and secreted genes was curated from Gene Bank and used to filter DNA microarray data from 304 breast tumor samples (37 node positive), 111 normal breast tissue samples, 15 unaffected lymph node, and 189 samples from 6 unaffected organ sites in the area surrounding the axillary nodes and those involved in clearance and toxicity. Five genes, CA12, CEACAM6, CXCL9, CXCL10 and MMP9, were identified with high expression in breast cancer including lymph node positive tumors, but low expression in the normal tissues surveyed (FIGS. 1A-1B, 4A-4D). Since CXCL9, CXCL10 and MMP9 products are secreted, and CEACAM6 had significant expression in the lung, CAXII was selected for validation. Also, CAXII was intriguing because of the potential for development of probes targeting the carbonic anhydrase catalytic site using sulfonamide-based inhibitors as imaging probes, which would target both CAXII and CAIX.

For validation of protein expression, immunohistochemistry (IHC) of CAIX and CAXII was performed on a tissue microarray (TMA) containing 50 normal breast tissue samples, 50 ductal carcinoma in situ, 50 invasive ductal carcinomas without metastasis, 50 invasive ductal carcinoma with metastasis, and 50 lymph node macrometastases. As shown in Table 1, positive staining of CAIX and CAXII was observed in the ductal epithelium of 73.9% and 100% of normal breast tissue samples, respectively. These markers were not present in normal breast stroma. CAIX and CAXII staining was distributed in the cell membranes of tumor tissues. Lymph node metastases samples (44%) were positive for both CAIX and CAXII and all of the positive lymph nodes were found to express either CAIX or CAXII. Tumor heterogeneity was found in 28.6% and 35% for CAIX and CAXII, respectively.

TABLE 1

Expression of CAIX and CAXII in normal breast and breast cancer patients

|  | CA9 | CA12 | Combination |
| --- | --- | --- | --- |
| Normal | 73.9% | 100% | 100% (n = 7) |
| DCIS | 71.4% | 81.3% | 100% (n = 9) |
| IDC without Mets | 55.8% | 78.7% | 100% (n = 28) |
| IDC with Mets | 56.5% | 80.4% | 93% (n = 26) |
| LN Macro Mets | 71.4% | 75.5% | 100% (n = 31) |

Mammaglobin A is expressed in 45% of LN macrometastases on breast TMA. An analysis of expression of all three of these markers on our TMA shows that 100% of the samples LN macrometastses express at least one of the three markers, 31% express only one, 51% express two, and 18% express all three markers. Therefore, a combination of CAIX, CAXII and mammaglobin markers can be used as suitable targets for imaging agents for early diagnosis of metastatic breast cancer in lymph nodes.

Example 2

Cell Models and In Vitro Studies

Materials and Methods

Cell Culture: A breast cancer cell line that expresses luciferase, MDA-mb-231-luc, (Baggett, B. et al. Mol Imaging 3:324-332 (2004)) was grown in RPMI 1640 containing 10% fetal bovine serum (Life Technologies), 0.03% L-glutamine, 100 units/mL penicillin, 100 μg/mL streptomycin and 300 μg/ml G418 (Mediatech) in 5% CO2 at 37° C.

Generation of stably transfected MDA-mb-231 cells bearing the CA12 gene: pCMV6-XL5 containing homo sapiens CA12 was purchased (Origene) and it was subcloned to pCDNA3.1-Zeo (Invitrogen) containing Zeocin™ as a selectable marker for mammalian cells. Briefly, pCMV6-XL5 and pCDNA3.1-Zeo were digested by NotI and XbaI (Invitrogen) and the digested fragment was inserted into NotI/XbaI restriction sites of digested pCDNA3.1-Zeo vector and the ligated mixture was transformed into competent cells of E. coli DH5α.

To identify the optimal concentration for selection, a range (50-1000 μg/ml) of Zeocin™ (Invitrogen) was tested on MDA-mb-231 cells. MDA-mb-231 cells expressing luciferase were transfected with 5 μg of pCDNA3.1-Zeo containing CA12. In response to zeocin, massive cell death was observed after ~5 days. After 2 weeks, resistant colonies appeared. Large colonies were selected and transferred to individual plates. The clone with the highest expression of CA12 was determined using qRT-PCR as previously described (Morse, D. L. et al. Anal Biochem 342:69-77 (2005)). RNA was extracted from each clone using an RNA extraction kit (Qiagen). CA12 specific primer sets were designed using Gene Runner Software for Windows version 3.05: forward, 5'-CTGGCATCATGTATTTAGGGGC-3' (SEQ ID NO:1) and reverse, 5'-GAGTTGCGCCTGTCAGAAAC-3' (SEQ ID NO:2). β-actin was used for normalization. A clone with the highest expression was selected and maintained in medium containing 300 µg/ml of G418 and 800 µg/ml of zeocin.

Immunocytochemistry (ICC) and fluorescence microscopy: To verify expression of CAXII in engineered cells, two sets of MDA-mb-231 (as a negative control) and MDA-mb-231/CAXII cells (each 1×10$^4$) were plated onto glass coverslips placed at the bottom of culture wells and incubated for 16 h. Cells were fixed with a 1:1 mixture of cold methanol and acetone, air dried for 20 min, blocked with 3% BSA and 0.2% saponin in PBS for 1 hour at room temperature and incubated with 1:50 CAXII antibody (Sigma-Aldrich) for 1 h. Plates were then washed (3 times, 5 min each) with PBS containing 0.2% saponin, and incubated with 1:2000 secondary antibody (Alexa-Fluor 488 goat anti-mouse IgG, Invitrogen). After three washes, coverslips were mounted using mounting medium with DAPI, 4,6-diamidino-2-phenylindole (Vector Laboratories, Inc.). Samples were viewed in the Analytic Microscopy Core Facility at Moffitt Cancer Center using an automated Zeiss Observer Z.1 inverted microscope with 40×/1.3NA oil immersion objectives through narrow bandpass DAPI, FITC/A488 Chroma filter cubes, Nomarski Differential Interference Contrast polarizing, and analyzing prisms. Images were produced using the AxioCam MRm CCD camera and Axiovision version 4.6 software suite (Carl Zeiss Inc.).

Conjugation of antibodies to dye and fluorescence microscopy studies: A mixture of 10 µg anti-human CAIX monoclonal antibody (mAb) (Clone 303123, R&D systems) was incubated with 10 µg VivoTag-S® 680 (VisEn Medical) at room temperature for 1 hour. The immunogen for this antibody is rhCA9; accession #NP_001207; aa 59-414, which corresponds to the N-terminus and the extracellular domain. The conjugate was purified with a Sephadex® G25 column (Roche) and eluted into a sterile tube. Protein (A280) and dye (A680) absorbance was determined using an ND-1000 spectrophotometer (NanoDrop) and used to confirm the number of fluorophore molecules conjugated to each antibody molecule. The conjugate was termed CA9Ab-680.

The same procedure was used for conjugation of CAXII mAb (Clone 315602, R&D system) to the dye. The immunogen for this antibody is rhCA12; accession #NP_001209; aa 25-291, which corresponds to the N-terminus and the extracellular domain. The conjugate was termed CA12Ab-680.

To verify that CA9Ab-680 and CA12Ab-680 retained binding specificity, 1×10$^4$ MDA-mb-231 cells (constitutively expressing CAIX and not expressing CAXII) and the same number of MDA-mb-231/CAXII (engineered cells to express CAXII) were seeded and incubated for 16 hours, then fixed as described above. The fixed cells that constitutively express CAIX were incubated with 0.5 µg/µl CA9Ab-680, and both cell lines were incubated with 0.5 µg/µl CA12Ab-680. Cells were also incubated with 5.0 µg/mL of wheat germ agglutinin (WGA), Oregon Green 488 conjugate (Invitrogen) for 30 min. After three washes, coverslips were mounted using mounting medium with DAPI. Micrographs were acquired at 200 Hz in the Analytic Microscopy Core at Moffitt Cancer Center using a Leica DMI6000 inverted microscope and TCS SP5 tandem confocal scanner, through a 63X/1.40NA Plan Apochromat oil immersion objective lens (Leica Microsystems) with triple photomultiplier tube detectors. Lasers, 405 diode (DAPI/Lysotracker Blue), 488 tunable argon (Green dye) and 543 diode (Rhodamine), were applied to excite the samples and a tunable emission filter was used to eliminate crosstalk between fluorochromes. LAS AF software version 2.1.0 (Leica Microsystems) was used to acquire and save the images using no compression of the original files.

Statistics: Data are represented as mean±s.d. and Student's t-test was used to determine significance.

Results

Cells were needed that express CAIX and CAXII for in vitro as well as in vivo studies. MDA-mb-231 breast cancer cells constitutively express CAIX (Brennan, D. J. et al. Clin Cancer Res 12:6421-6431 (2006); Robey, I. F. et al. Neoplasia 7:324-330 (2005); Li, Y. et al. Cancer Invest 27:613-623 (2009)), but do not express the CA12 gene (and presumably the protein) as determined by qRT-PCR. Therefore, MDA-mb-231-luc cells were engineered to stably express CAXII as confirmed by qRT-PCR and ICC.

Monoclonal antibodies (mAbs) from R&D Systems that bind to the extracellular domain of CAIX and CAXII, respectively, were determined to be highly target specific by Western analysis and ICC, and were conjugated to a near-infrared (NIR) fluorescent dye (VivoTag-S® 680, VisEn). To verify the selectivity of the CAIX antibody-dye conjugate (CA9Ab-680), ICC was performed using the molecular probe on the CAIX constitutively expressing MDA-mb-231 cells and MCF-7 cells which do not express CAIX in normoxia condition as a negative control (Robey, I. F. et al. Neoplasia 7:324-330 (2005)). For CA12Ab-680, ICC was performed using MDA-mb-231 cells engineered to express CAXII (MDA-mb-231/CAXII) and the parental cells as a negative control. CA12Ab-680 bound only to expressing cells. Hence, the conjugated agents retained specificity for CAIX and CAXII proteins.

Example 3

In Vivo and Ex Vivo Selectivity Studies

Materials and Methods

Tumor xenograft studies: To study selectivity of the CA9Ab-680 imaging probe, female nu/nu mice 6-8 weeks old (Harlan Sprague Dawley, Inc.) were implanted with 5×10$^6$ MDA-mb-231 (as CAIX expressing cells) in the right mammary fat pad (MFP). To study CA12Ab-680, the same procedure was done, except that MDA-mb-231/CAXII (as CAXII expressing cells) were implanted in the right MFP and MDA-mb-231 (as non-expressing cells) in the left MFP. Tumor volume was determined with calipers using the formula: volume=(length×width)/2. Once tumors reached 500-800 mm$^3$, 50 µg CA9Ab-680 in 100 µL sterile saline, was injected into the tail vein. In vivo fluorescence images were acquired using an IVIS 200 small animal imaging system (Caliper LifeSciences) using a 615-665 nm excitation filter and a 695-770 nm emission filter. According to the manufacturer, the excitation maxima of unconjugated VivoTag-S® 680 dye is 673±5 nm and the emission maxima is 691±5. Living Image 3.2 Software was used to draw regions of interest (ROIs) over the tumors to determine the mean tumor surface radiance (photons/sec/steradian/cm$^2$). Autofluorescence background was subtracted by determining the mean tumor fluorescence signal prior to injection.

Ex vivo studies: One half of each excised tumor from animals was fixed in formalin and embedded in paraffin, the other half placed in Tissue-Tek Optical Cutting Temperature (OCT) cryoembedding media (Sakura Finetek) and snap frozen in liquid nitrogen. For histology, formalin fixed sections (5 µm) were stained with hematoxylin and eosin (H&E). Frozen sections were stained with the CA9Ab-680 and CA12Ab-680 using the ICC protocol described above. Sections were also stained with mammaglobin-A primary antibody as described above for TMAs.

Statistics: Data are represented as mean±s.d. and Student's t-test was used to determine significance.

Results

To study the selectivity of the CA9Ab-680 in vivo, MDA-mb-231 cells that constitutively express CAIX were used to form a positive MFP tumor in nude mice. Since CAIX is expressed under hypoxic conditions, all tumors may express CAIX, including small metastases which may not have established vasculature. Therefore, a blocking experiment was used to determine specificity, where unlabeled CAIX mAb was added prior to CA9Ab-680.

For CA12Ab-680, MDA-mb-231/CAXII cells were used for generating the positive tumor in the right MFP, and parental cells were used for the negative left MFP tumor. After tumor growth to approximately 500-800 mm$^3$ in volume, agent was intravenously (i.v.) injected. CA9Ab-680 was retained in the CAIX positive MDA-mb-231 tumor 24 hours after injection, and that after blocking with unlabeled CAIX mAb, the amount of probe retained in the tumor was decreased. After blocking, the probe-related fluorescence signal decreased by 1.7 times relative to the unblocked tumor. The MDA-mb-231/CAXII tumor also retained high levels of the CA12Ab-680 compared to the CAXII negative xenograft. Expression in the CAXII positive tumor was quantified as having a 7.0±1.0 s.d. (n=3, p<0.001) fold greater fluorescence compared to the negative tumor. These results demonstrate the in vivo targeting specificity of the molecular probes.

For further confirmation, an ex vivo analysis was performed. Sections of flash-frozen tumors were stained with the probes, a nuclear stain, (DAPI), and a cell-surface/cytoplasmic stain, wheat germ agglutinin (WGA), and were imaged using confocal microscopy. CAIX staining was observed in the positive tumor, and was reduced by blocking with unlabeled mAb. CAXII staining was only observed in tumors from the positively expressing cell line but not in the negative line. Ex vivo images of the corresponding center sections of the tumors confirmed the in vivo results and allow comparison of probe signal relative to target expression in adjacent sections by IHC and histology.

Example 4

Pharmacokinetics and Biodistribution Studies

Materials and Methods

Pharmacodynamics and biodistribution studies: Pharmacodynamics studies were performed by imaging at various time points. For biodistribution studies, mice were imaged and euthanized at 24 h and 48 h post-injection, tissues excised, rinsed with PBS, blotted dry, and then imaged ex vivo in the IVIS-200. A center slice cut from the tumor was imaged and the remaining halves were formalin fixed and fresh frozen, respectively, as described below. Mean surface radiance was determined for each tumor and organ. Autofluorescence background was subtracted using measurements from comparable tissues from an untreated animal.

Statistics: Data are represented as mean ±s.d. and Student's t-test was used to determine significance.

Results

Figure 2A:
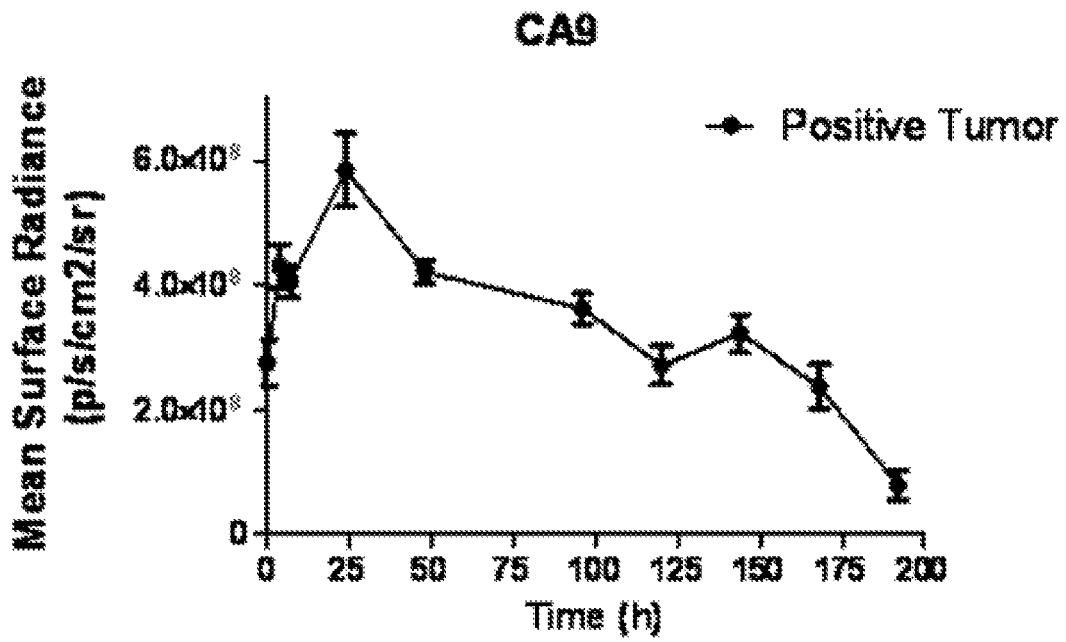
FIGS. 2A and 2B are graphs showing mean surface radiance (photons/sec/cm$^2$/steradian) as a function of time (hrs) for CA9Ab-680 (FIG. 2A) and CA12Ab-680 (FIG. 2B) antibodies in positive (●) and negative (■) mammary fat pad (MFP) tumors. Note that the peak signal in the positive Carbonic anhydrases 9 (CAIX) and 12 (CAXII) tumors is 24-hours post-injection, and that the agents are nearly cleared after 8 days. Data represent mean±s.d.
Figure 2B:
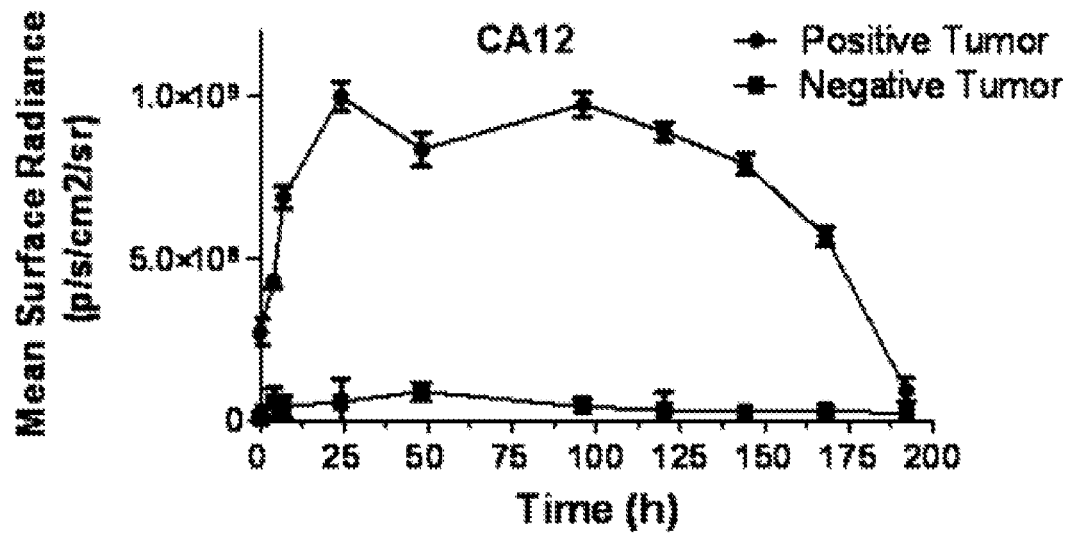

To evaluate the pharmacodynamics of probe uptake and clearance in the tumors, CA9Ab-680 and CA12Ab-680 were intravenously (i.v.) injected and images acquired at intervals from 5 minutes to 8 days post injection (FIG. 2A and 2B). Fluorescence signal in positive tumors increased to a maximum at 24 hours following injection of both probes, and signal slowly cleared until approximately 7 days post-injection. Fluorescence signal in CAXII negative tumors increased slightly for about 24 hours and slowly cleared over the following 5 days.

Figure 2C:
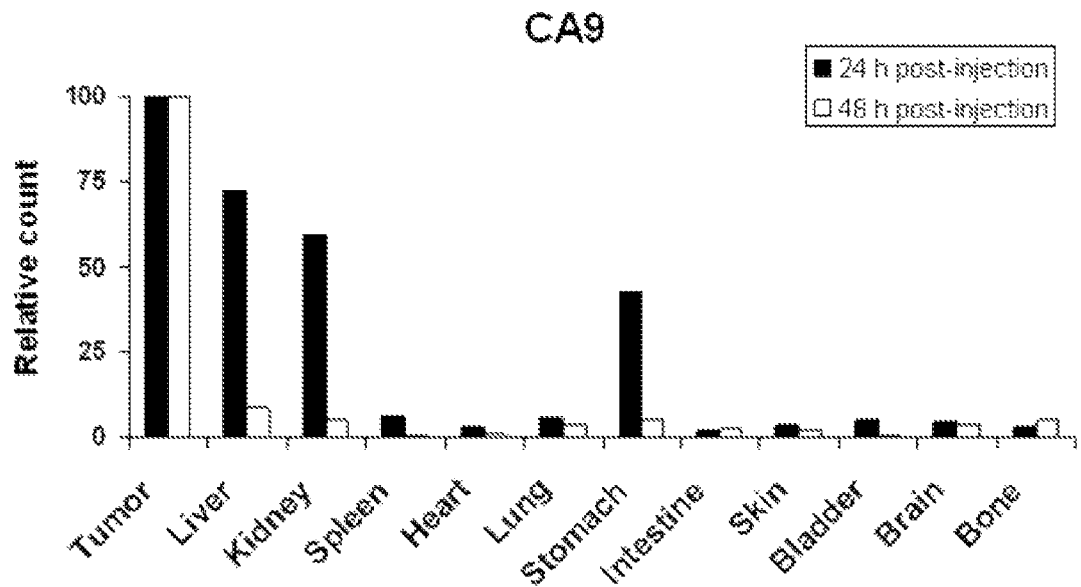
FIGS. 2C and 2D are bar graphs showing biodistribution (relative count) of CA9Ab-680 (FIG. 2C) and CA12Ab-680 (FIG. 2D) in tumors (FIG. 2C) or positive and negative tumors (FIG. 2D), liver, kidney, spleen, heart, lung, stomach, intestine, skin, bladder, brain, and bone 24 hours (solid bars) and 48 hours (open bars) post-injection. The values were normalized as percentage of the highest signal.
Figure 2D:
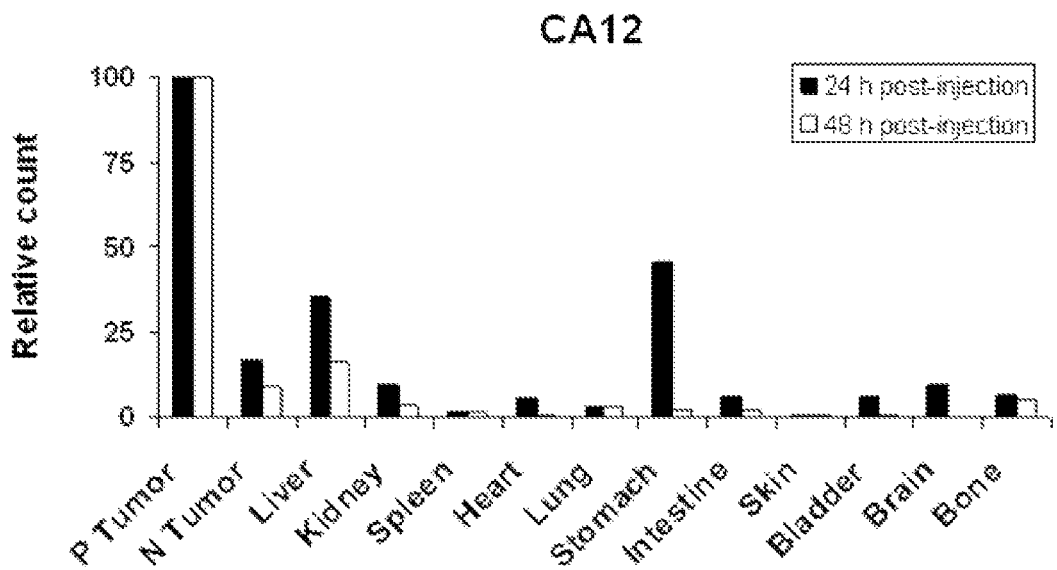

For biodistribution studies, mice bearing tumors were injected with probe, and tissue distribution of fluorescence signal determined after removing tumors and organs at 24-hours and 48-hours post-administration (FIG. 2C and 2D). Twenty four hours post-injection, CA9Ab-680 and CA12Ab-680 retained at relatively high levels in the positive tumor relative to a corresponding negative tumor and other organs. However, the CAIX probe was elevated in liver, kidney and stomach and the CAXII probe was elevated in the liver and stomach. After 48 hours, probe had nearly cleared from all tissues except for positive tumors.

Example 5

Detection of Malignant Cells in ALNs Using CA9Ab-680 and CA12Ab-680 Imaging Probes Materials and Methods Metastases to ALNs of mouse model: For the CA9Ab-680 study, 5×10$^6$ luciferase expressing MDA-mb-231 cells were implanted into the right MFP of 6-8 weeks old female nu/nu mice. Eight to nine weeks later, bioluminescence imaging was used to follow metastasis formation in the ALN. Animals were anesthetized and 300 µl of D-luciferin potassium salt (GoldBio) was introduced via intraperitoneal (i.p.) injection. Five minutes after the injection, a bioluminescence image was acquired using standard bioluminescence settings on the IVIS 200. The same protocol was used for CA12Ab-680, except that MDA-mb-231 cells that express both luciferase and CAXII were used.

To determine agent sensitivity, precise numbers of cells were injected into ALNs using ultrasound image guidance. Female nu/nu mice (6-8 weeks old) were anesthetized with 3-4% isoflurane using a nose-cone manifold and restrained on the stage of a VEVO® 770 high-resolution small animal ultrasound imaging system (VisualSonics) using tape; ultrasound gel was applied to the area over the right axillary node; the 40 MHz ultrasound probe was placed in the probe guide and the node located by mechanically adjusting the probe guide to resolve the nodes; and a 1 cc syringe with a 29 gauge needle was loaded with 500 to 100,000 cells in a 20 µL volume of 1:1 matrigel and sterile PBS and positioned in the needle guide so that the end of the needle could be moved into the node and cells injected. Ultrasound images were acquired at the time of each injection. Four hours after injection of cells, animals were imaged using bioluminescence as described above. Twenty-four hour after injection of cells, 30 µg of agent was injected into the mammary fat pad proximal to axillary nodes, and fluorescence imaging was performed using the IVIS-200 as described above for pharmacodynamics and biodistribution studies.

Statistics: Data are represented as mean±s.d. and Student's t-test was used to determine significance.

Results

To investigate whether the CAIX and CAXII molecular imaging probes can be delivered through the lymphatics and are selectively retained in positive ALNs, the MDA-mb-231-luc spontaneous metastasis model was used. After injecting cells in the MFP, ALN metastases were observed after 6-8 weeks by bioluminescence imaging. Probe was then injected peritumorally into the MFP and observed to traverse through the MFP into the lymph node within 4 hours. At 24 h post-injection, a strong fluorescence signal was obtained from the area of the ALN corresponding to a metastasis positive for the marker, and the probe had mostly cleared from the MFP. A specific and durable fluorescence signal was observed in target positive metastases out to at least 48 hours post-injection, long after completely clearing from the MFP. Probe was not retained in ALN metastases that did not express the target marker.

Figure 3A:
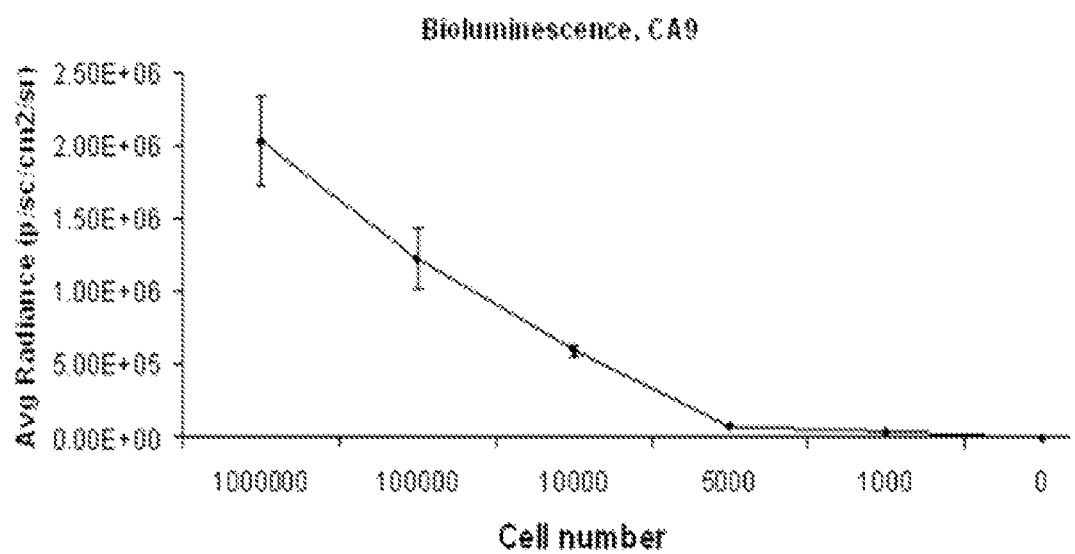
FIGS. 3A and 3B are graphs showing bioluminescence (average radiance (photons/sec/cm$^2$/steradian)) of MDA-mb-231 cells expressing CAIX (FIG. 3A) or CAXII (FIG. 3B) four hours after injection into ALN of 6-8 weeks old female nu/nu mice as a function of the number of cells injected (1,000,000, 100,000, 10,000, 5,000, 1,000, or 0).
Figure 3B:
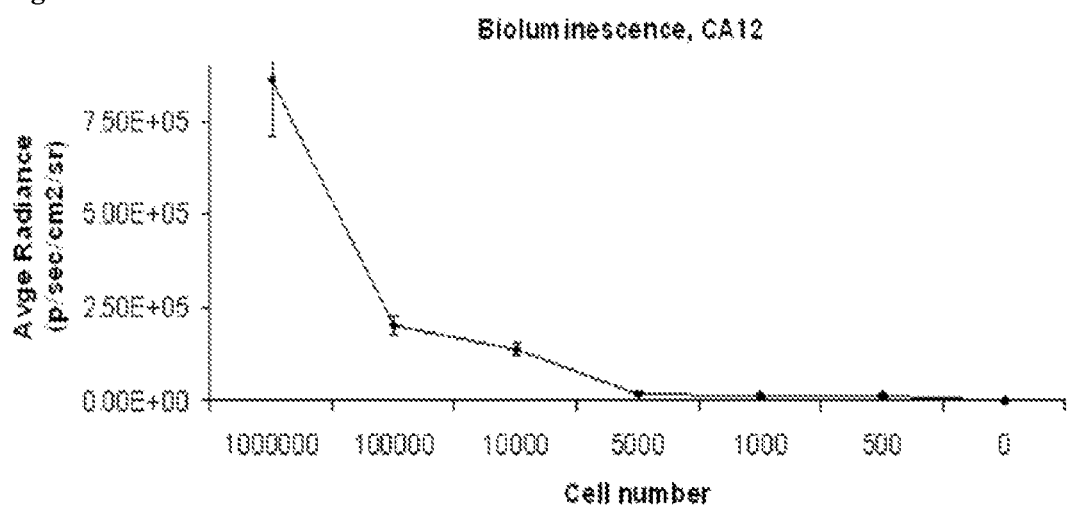
Figure 3C:
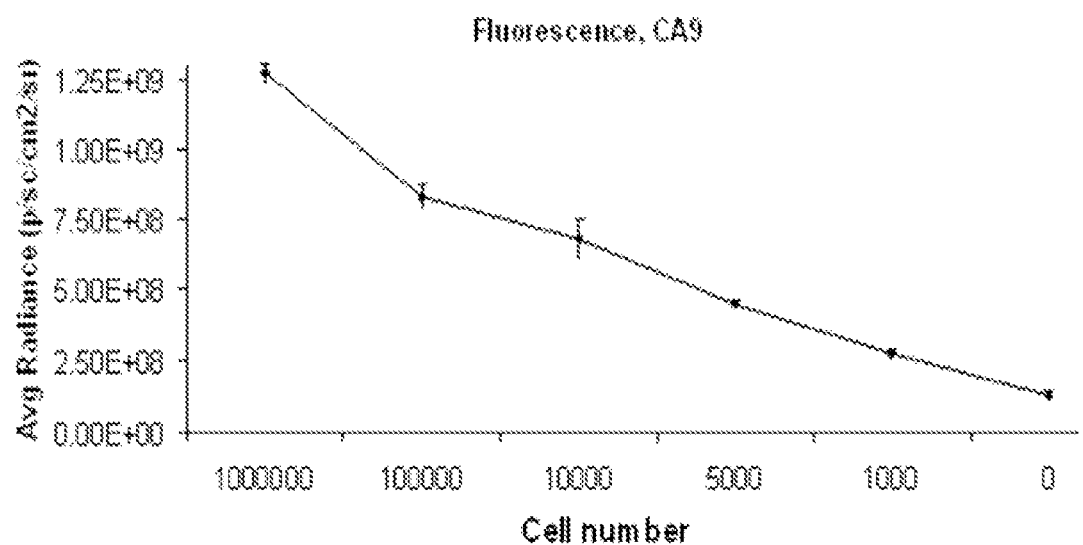
FIGS. 3C and 3D are graphs showing fluorescence (average radiance (photons/sec/cm$^2$/steradian) 24 hours after injection of CA9Ab-680 (FIG. 3C) or CA12Ab-680 (FIG. 3D) into MFP of the mice of FIGS. 3A and 3B as a function of the number (1,000,000, 100,000, 10,000, 5,000, 1,000, or 0) of MDA-mb-231 cells expressing CAIX or CAXII injected into ALN. All data represent mean±s.d. of pixel values within the ROIs.
Figure 3D:
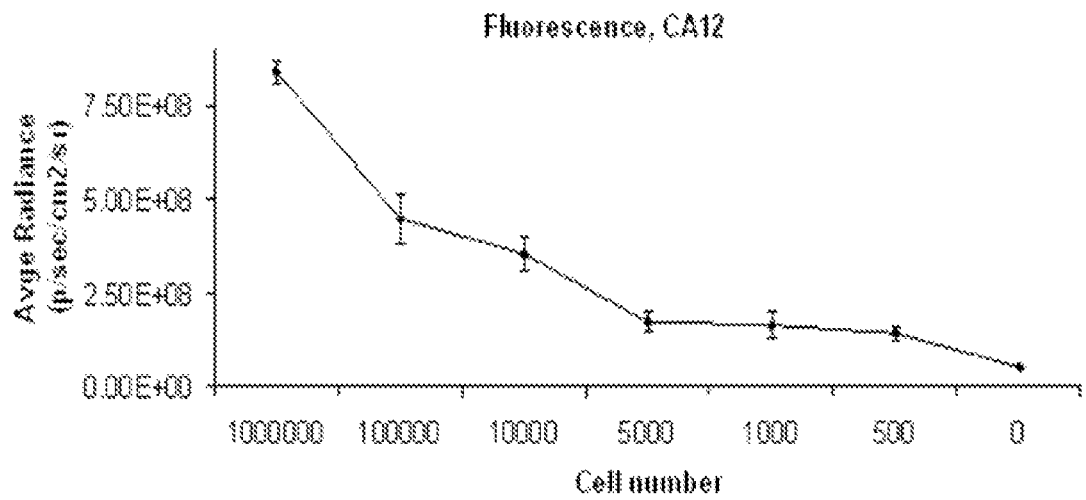
Figure 4A:
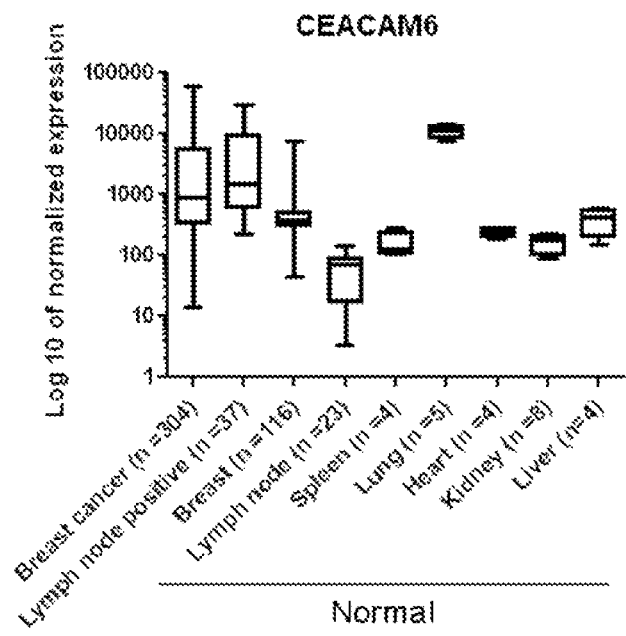
FIGS. 4A to 4D are bar graphs showing CEACAM6 (FIG. 4A), CXCL9, (FIG. 4B), CXCL10 (FIG. 4C), and MMP9 (FIG. 4D) mRNA expression (Log 10 of normalized expression) in breast cancer, lymph node positive, breast, lymph node, spleen, lung, heart, kidney, and liver samples. Data are represented as mean±s.d. Note the Log 10 scale.
Figure 4B:
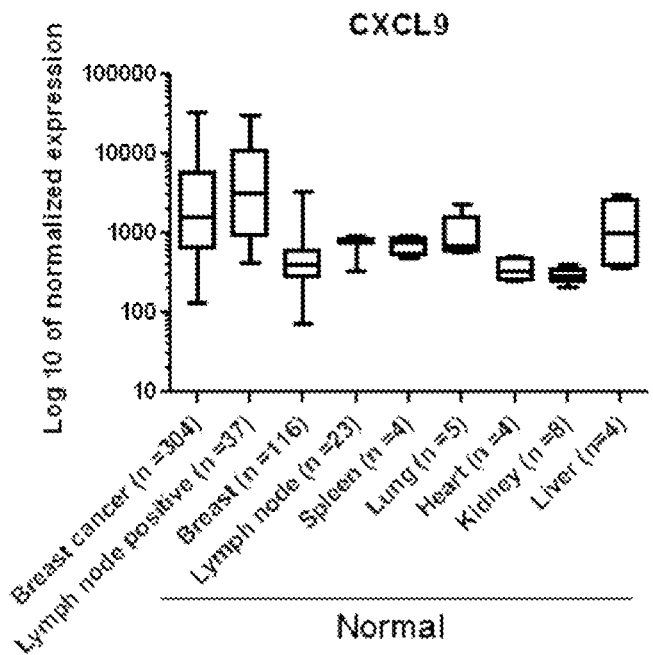
Figure 4C:
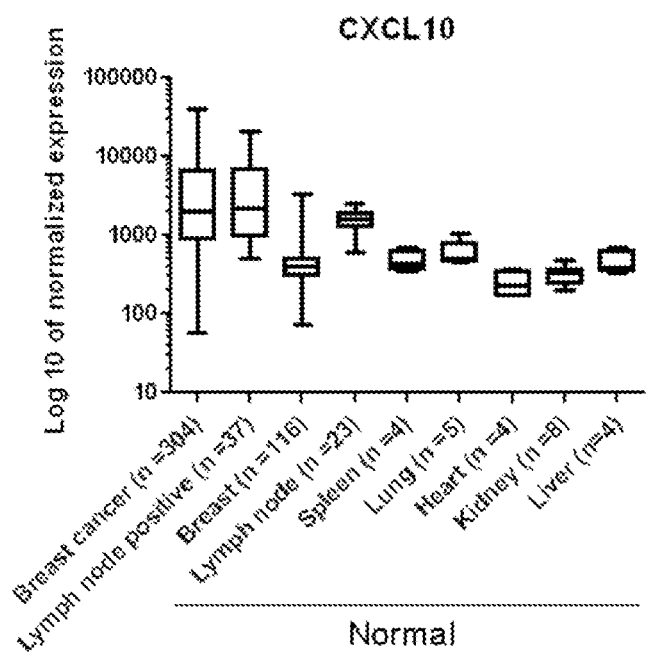
Figure 4D:
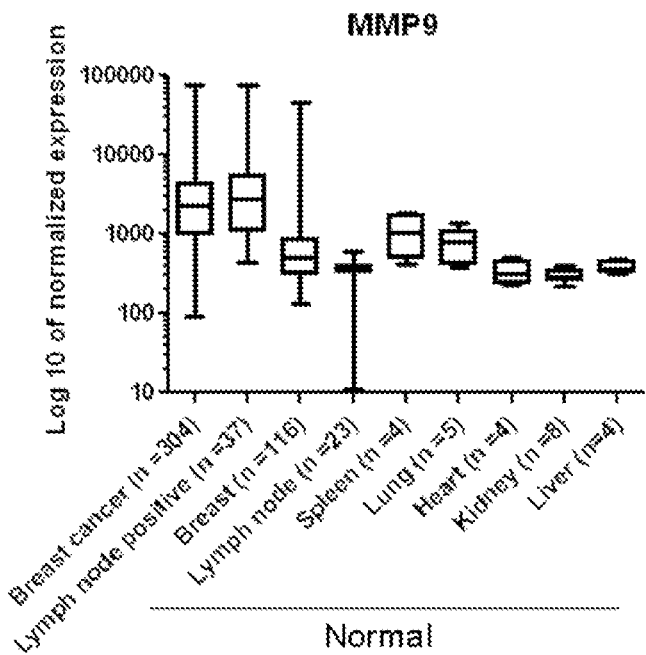

Agent selectivity and sensitivity for positive lymph nodes was also measured using an orthotopic model of lymph node metastasis. A range in number of MDA-mb-231/Luc cells that constitutively express CAIX but do not express CAXII, and a range of MDA-mb-231/Luc/CAXII cells (500 to 1 million) were directly injected into the ALN using ultrasound image guidance. For confirmation of successful cell implantation, cells were detected by bioluminescence imaging four hours after implantation. Twenty four hours after cell implantation, CA9Ab-680 and CA12Ab-680 were delivered by MFP injection and fluorescence images were acquired 24 hours after injection. Bioluminescence and fluorescence signals were quantified by drawing a region-of-interest (ROI) surrounding the tumor cells in the ALN. As expected, signal intensities for both bioluminescence and fluorescence decreased with cell number (FIGS. 3A-3D). With fluorescence, the CA12Ab-680 probe detected as few as 500 cells above background and CA9Ab-680 detected as few as1000 cells (FIG. 3C-3D). When CA12Ab-680 was injected into the MFP of animals that were sham injected into the axillary lymph node with matrigel and PBS, probe was not retained at the 24 hour time point.

In conclusion, either CAIX or CAXII are expressed in 100% of lymph node metastasis from patients with breast cancer. CAIX and CAXII targeted molecular imaging probes were developed for non-invasive in vivo imaging and detection of breast cancer metastases in ALNs using small animal models. These imaging probes detected tumor cells in ALNs with high sensitivity. This targeted imaging strategy has potential for future translation into the clinic for ALN assessment and intraoperative surgical guidance as well as monitoring alteration in CAIX/CAXII expression as an indicator of treatment response. In the future, the agents may be improved by development of small targeting peptides and agents with theragnostic capability.

Example 6

CAIX and CAXII are Cell-Surface Markers for Non Small-Cell Lung Cancer (NSCLC)

Figure 5A:
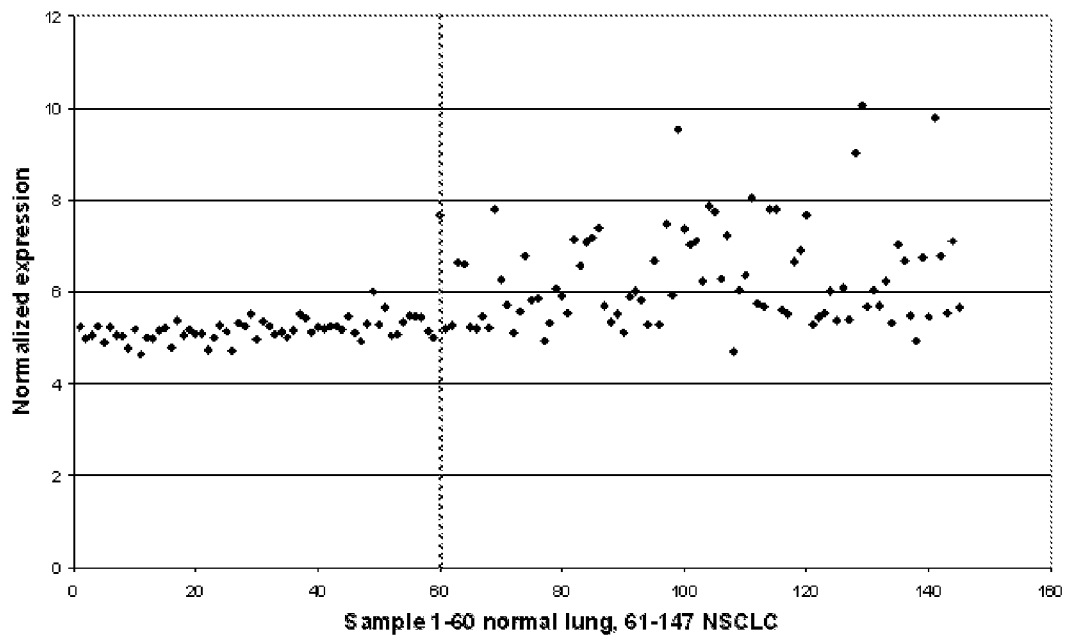
FIGS. 5A and 5B are plots showing CAIX (FIG. 5A) and CAXII (FIG. 5B) expression ($\log_2$ normalized expression) in normal lung (samples 1-60) and adjacent non small-cell lung cancer (NSCLC) (samples 61-147) samples.
Figure 5B:
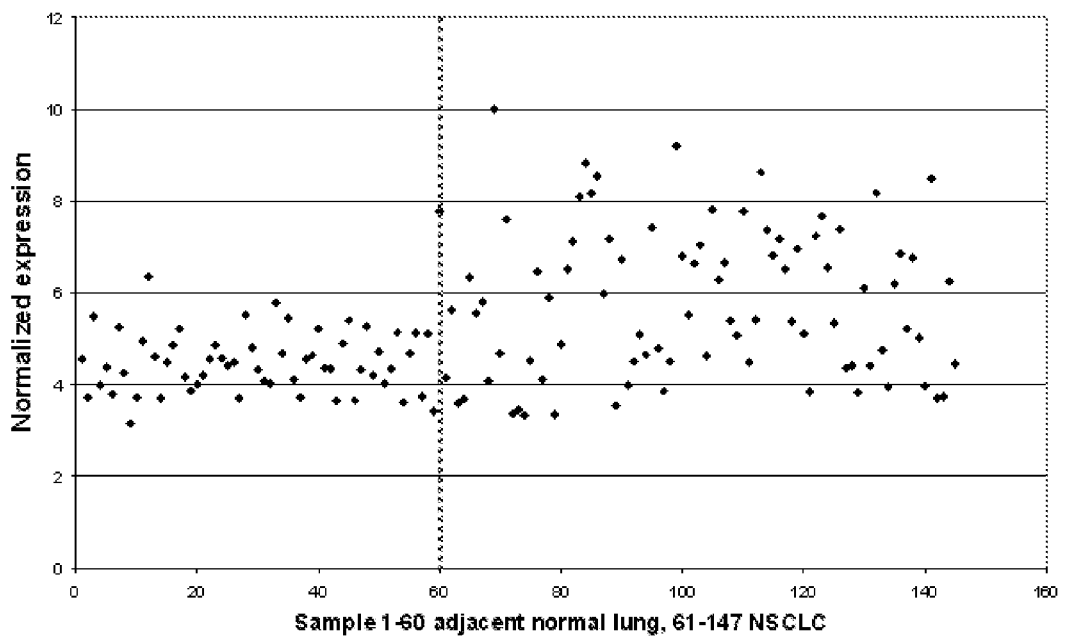

Expression profiling of CAIX and CAXII in 147 NSCLC patient samples, 87 from NSCLC tumors and 60 from adjacent normal lung, are shown in FIG. 5A and 5B. NCBI Gene Expression Omnibus (GEO) dataset GSE19188, shows that CAIX is expressed higher in 45% of NSCLC tumors compared to the highest expression observed in any adjacent normal tissue in the dataset, and that CAXII is expressed higher in 39% of NSCLC tumors (FIGS. 5A and 5B). Hence, these markers may be general markers for cancer and imaging probes against these markers may be used for detection of cancer of the lung as well as breast, and possibly other cancer types as well.

Example 7

Mammaglobin-A Expression in Patient Tissue Samples

Materials and Methods

DNA microarray analysis: Affymetrix expression data for the mammaglobin-A gene (SCGB2A2) in patient tissue samples were compiled from publicly available datasets. The CEL files for the tumor samples were downloaded from the NCBI Gene Expression Omnibus (GEO) database (ncbi.nlm.nih.gov/projects/geo/index.cgi), data series GSE2109. Normal tissue data were from the GEO data series GSE7307, Human Body Index. The CEL files were processed using the MAS 5.0 algorithm (Affymetrix, Santa Clara, Calif.) and screened through a rigorous quality control panel to remove samples with a low percentage of probesets called present by the MAS 5 algorithm, indicating problems with the amplification process or poor sample quality; high scaling factors, indicating poor transcript abundance during hybridization; and poor 3'/5' ratios, indicating RNA degradation either prior to or during processing. The remaining samples were normalized to the trimmed average of 500 in the MAS 5 algorithm before comparison of the expression values across tumors and normal samples.

Immunohistochemistry (IHC) of Tissue Mircroarray (TMA): A TMA was constructed at the Moffitt Tissue Core, containing 50 normal breast tissue, 50 ductal carcinoma in situ, 50 invasive ductal carcinomas without metastasis, 50 invasive ductal carcinomas with metastasis and 50 lymph node with macrometastases of breast carcinoma. The same method was previously reported by our group for construction of a Ewing sarcoma TMA (Sharma, P. et al. *Chem Mater* 20:6087-6094 (2008)), except the breast TMA has only one sample per case. Mouse anti-mammaglobin-A mAb, 1:50, (Clone 304-1 A5, Thermo Scientific, Rockford, Ill.) was used for staining Positive staining was arbitrarily set as membranous (partial or complete) and cytoplasmic immunoreactivity in greater than or equal to 5% of tumor cells. Results were recorded as positive or negative.

Statistics: Data are represented as mean±s.d. and the t-test was used to determine significance.

Results

Figure 6:
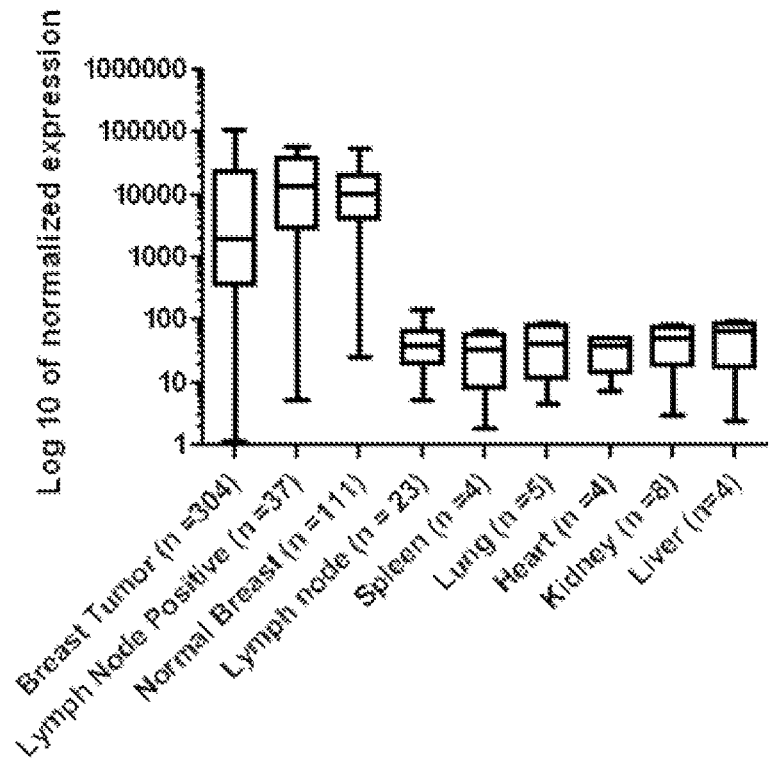
FIG. 6 is a bar graph showing Mammaglobin-A mRNA expression ($\log_{10}$ of normalized expression) in breast cancer, lymph node positive, breast, lymph node, spleen, lung, heart, kidney, and liver samples. Data are represented as mean±s.d.

Several studies have demonstrated high expression of mammaglobin-A in breast cancer (Span, P. N. et al. *Br J Cancer* 89:271-276 (2003)). For further confirmation and to characterize mRNA expression in patient tissue samples, including lymph node metastases and normal tissues, publicly available DNA microarray data sets were analyzed. Mammaglobin-A mRNA was highly and generally expressed in breast tumors, breast cancer lymph node metastases and in normal breast (FIG. 6). A high percentage (83%) of lymph node metastases expressed mammaglobin-A. In contrast, mammaglobin-A was not expressed in normal lymph nodes. Also, other organs involved in toxicity or drug clearance, i.e., liver, kidney, heart, lung and spleen did not express mammaglobin-A mRNA.

To determine mammaglobin-A protein expression in patient samples, immunohistochemistry (IHC) was performed on a breast cancer tissue microarray containing 250 samples. Positive staining was observed in the ductal epithelium of 63% of normal breast tissues, 80% DCIS, 53% invasive ductal carcinoma without metastasis, 43% invasive ductal carcinoma with metastasis and 45% lymph node with macrometastasis of breast cancer.

Example 8

ZR-75.1 Breast Cancer Cells Express Mammaglobin-A

Materials and Methods

Stable transfection of ZR-75.1 cells: The cells were transfected with 5 µg of pLenti PGK Blast V5-LUC luciferase containing vector (Addgene, Cambridge, Mass.) using the ViraPower lentiviral expression system (Invitrogen, Carlsbad, Calif.). In response to blasticidin (5 ug/ml), resistant colonies appeared. Clones were screened by adding medium containing 150 µg/ml D-luciferin potassium salt (GoldBioTechnology, St. Louis, Mo.) to the cells and the light detected by a Victor X4 2030 multiple plate reader (PerkinElmer, Waltham, Mass.).

Cell culture: Mammaglobin-A expressing ZR-75.1 (Robey, I. F. et al. *Neoplasia* 7:324-330 (2005); Goonewardene, T. I. et al. *Microsc Res Tech* 59:41-48 (2002); Ivanov, S. et al. *Am J Pathol* 158:905-919 (2001)) and non-expressing MDA-mb-231 (Ivanov, S. et al. *Am J Pathol* 158:905-919 (2001)) were obtained from and cultured according to ATCC recommendations.

Quantitative real-time RT-PCR: Mammaglobin-A primers were designed using Gene Runner Software for Windows version 3.05: forward, 5'-CTTCTTCAAGAGTTCATA-GACGAC-3' (SEQ ID NO:3) and reverse, 5'-TGCTCAGAGTTTCATCCGTTTG-3' (SEQ ID NO:4). β-actin was used for normalization as described in our previous study (Sevick-Muraca, E. M. et al. *Radiology* 246:734-741 (2008)).

Results

ZR-75.1 breast cancer cells endogenously express mammaglobin-A (Robey, I. F. et al. *Neoplasia* 7:324-330 (2005); Goonewardene, T. I. et al. *Microsc Res Tech* 59:41-48 (2002); Ivanov, S. et al. *Am J Pathol* 158:905-919 (2001)) and MDA-mb-231 cells do not (Ivanov, S. et al. *Am J Pathol* 158:905-919 (2001)). To confirm this, mammaglobin-A mRNA expression was quantified by qRT-PCR in ZR-75.1 and MDA-mb-231 cells. As expected, mammaglobin-A was expressed in ZR-75.1 but not MDA-mb-231 cells. Western blot and immunocytochemistry (ICC) also confirmed protein expression.

Example 9

Antibody and MamAb-680 Characterization

Materials and Methods

Conjugation of antibody to dye: Fifteen µg human Mammaglobin-A specific mouse mAb (Zeta Corp., Calif., Sierra Madre) was incubated with 10 µg VivoTag-S 680 (VisEn Medical, Bedford, Mass.) and purified with a Sephadex G25 column (Roche, Indianapolis, Ind.). Protein (A280) and dye (A680) absorbance was determined using an ND-1000 spectrophotometer (NanoDrop, Wilmington, Del.) and used to confirm the number of fluorophore molecules conjugated to each antibody molecule.

Results

The specificities of three different mammaglobin-A monoclonal antibodies were evaluated for sensitivity and specificity by Western blot and ICC. A highly specific mAb (Zeta Corp.) was selected for conjugation to near-infrared dye (VivoTag-S 680). The mAb conjugated with near-infrared dye is referred to herein as MamAb-680. To evaluate the antibody-dye conjugation and to verify that MamAb-680 retained binding specificity, ICC was performed using only the dye-labeled primary antibody on the endogenously expressing ZR-75.1 cells, MDA-mb-231 cells engineered to express mammaglobin-A and the non-expressing MDA-mb-231 cells. MamAb-680 bound only to mammaglobin-A expressing cells. Hence, the conjugated agent retained specificity for mammaglobin-A protein.

Example 10

Mammaglobin-A is Expressed on the Cell-Surface

Mammaglobin-A is directly associated with the surface of breast cancer cells (Supuran, C. T. et al. *Bioorg Med Chem* 15:4336-4350 (2007)). As described above, permeabilized fixed cells were used for ICC. To verify cell-surface expression, ZR-75.1 cells were incubated with MamAb-680 at 4° C. Agent was observed at the cell surface co-localized with agglutinin dye. Western blots of membrane protein extracts of mammaglobin-A positive cells stained positive for mammaglobin-A protein.

Example 11

MamAb-680 Selectively Accumulates in Positive Tumors

Materials and Methods

Microscopic studies: Cells and tissues from positive and negative xenograft tumors were fixed with cold methanol: acetone and incubated with 1 µg/µl MamAb-680 and 5.0 µg/mL of WGA (Invitrogen, Carlsbad, Calif.) for 30 min. After washing, coverslips were mounted. Micrographs were acquired using a Leica DMI6000 inverted microscope and TCS SP5 tandem confocal scanner (Leica Microsystems, Germany).

Statistics: Data are represented as mean±s.d. and the t-test was used to determine significance.

Results

To determine the specificity of MamAb-680 targeting in vivo, ZR-75.1 and MDA-mb-231 cells were implanted in the right and left mammary fat pads (MFP) of female nude mice. After tumor growth to approximately 500-800 $mm^3$ in volume, MamAb-680 was intravenously (i.v.) injected.

ZR-75.1 tumors retained higher levels of the agent signal compared to MDA-mb-231. Fluorescence signal in the positive tumor was 8.6±0.8 s.d. (n=4, p<0.001) fold higher relative to the negative tumor. These results demonstrate the in vivo targeting specificity of MamAb-680.

To confirm the presence of mammaglobin-A protein in vivo, sections from flash-frozen tumors were stained with MamAb-680, a nuclear stain, 4',6-diamidino-2-phenylindole (DAPI), and a cell-surface/cytoplasmic stain, wheat germ agglutinin (WGA), and analyzed using confocal microscopy. Mammaglobin-A staining was observed in tumors from the positively expressing cell line but not in the negative line. Ex-vivo images of the corresponding center sections of the tumors confirmed MamAb-680 localization to the positive tumor relative to the negative tumor.

Example 12

Pharmacodynamics and Biodistribution of MamAb-680

Materials and Methods

Tumor xenograft studies: Female nu/nu mice 6-8 weeks old (Harlan Sprague Dawley, Inc., Indianapolis, Ind.) were implanted subcutaneously with 0.72 mg of estradiol (Innovative Research of America, Sarasota, Fla.). After two days, $5\times10^6$ cells were implanted in the mammary fat pad. Once tumors reached 500-800 mm$^3$, 50 µg MamAb-680, in 100 µL, saline, was injected into the tail vein. In vivo fluorescence images were acquired using an IVIS-200 small animal imaging system (Caliper LifeSciences, Hopkinton, Mass.) using a 615-665 nm excitation and a 695-770 nm emission filter. Living Image 3.2 Software was used to draw regions of interest (ROIs) over the tumors to determine the mean tumor surface radiance. Autofluorescence background was subtracted by determining the mean tumor fluorescence signal prior to injection. Pharmacodynamics studies were performed by imaging at various time points. For biodistribution studies, mice were euthanized at 24 h post-injection, tissues excised and imaged ex vivo in the IVIS-200.

Statistics: Data are represented as mean±s.d. and the t-test was used to determine significance.

Results

Figure 7A:
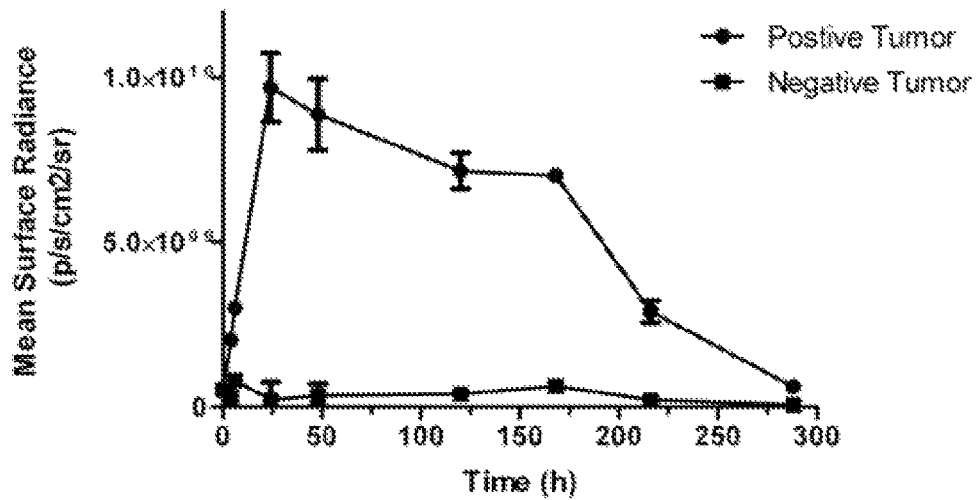
FIG. 7A is a graph showing mean surface radiance (photons/sec/cm$^2$/steradian) as a function of time (hrs) for Mammaglobin-A antibodies (MamAb-680) in positive (●) and negative (■) mammary fat pad (MFP) tumors. Data represent mean±s.d.

To assess the pharmacodynamics of tumor uptake and clearance, MamAb-680 was injected intravenously (i.v.) and images acquired at intervals from 5 min to 12 d post injection. Fluorescence signal increased for 24 h and then slowly decreased at later time-points (FIG. 7A). Elevation of fluorescence in the positive tumor relative to the negative tumor was detected from 4 h to 10 days after injection.

Figure 7B:
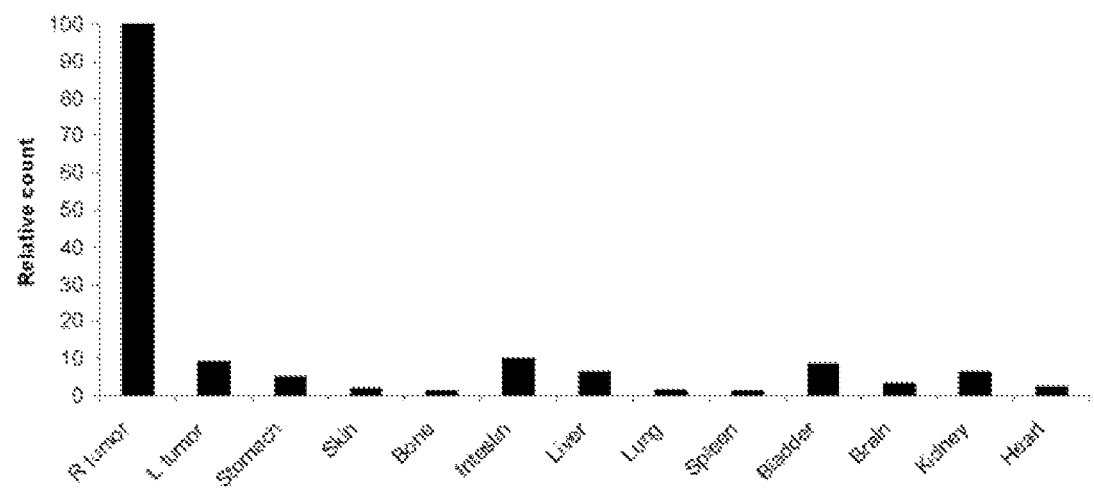
FIG. 7B is a bar graph showing biodistribution (relative count) of MamAb-680 in Mammaglobin-A positive and negative tumors, stomach, skin, bone, intestine, liver, lung, spleen, bladder, brain, kidney, and heart 24 hours post-injection.

For biodistribution studies, MamAb-680 was i.v. injected into mammaglobin-A positive and negative tumor-bearing mice and, 24 h later, the tumors and organs were removed and imaged ex vivo. Fluorescence was present in the positive tumor but agent was largely cleared from the negative tumor and other organs (FIG. 7B).

Example 13

MamAb-680 Detects Tumor Cells in Axillary Lymph Nodes

Materials and Methods

Tumor xenograft studies: see description in Example 12.

Orthotopic implantation of cells into ALN: A range of 100 to 100,000 ZR-75.1/Luc cells in a 20 µL volume of 1:1 matrigel and PBS were injected into the axillary lymph node using image guidance by a VEVO 770 ultrasound imaging system (VisualSonics, Toronto, Canada). Four h after injection of cells, 300 µl of 15 mg/ml D-luciferin potassium salt was introduced via intraperitoneal injection and bioluminescence images were acquired using an IVIS-200. Twenty-four h after injection of cells, 50 µg MamAb-680 was injected into the mammary fat pad proximal to ALN, and fluorescence imaging was performed.

Statistics: Data are represented as mean±s.d. and the t-test was used to determine significance.

Results

ZR-75.1 cells have not been reported to form ALN metastases. To determine this, $5\times10^6$ ZR-75.1/Luc cells were implanted into the right MFP of estrogen-pelleted mice. Three weeks after implantation, tumors were surgically removed. Two weeks later, the tumor had re-grown and bioluminescence imaging showed metastasis to the ALN. Hence, ZR-75.1 cells are a suitable model for ER+breast cancer lymph node metastasis.

To investigate whether MamAb-680 can be delivered through the lymphatics to selectively bind positive nodes, the agent was injected peritumorally into the MFP. At 24 h post-injection, the area of the ALN showed a strong fluorescence signal, which co-localized with the bioluminescence image of the luciferase expressing metastases. After imaging, the metastases was removed and the presence of cancer cells confirmed by H & E staining and pathological examination.

Agent selectivity was also determined for positive lymph nodes using an orthotopic model of lymph node metastasis. ZR-75.1/luc cells were directly injected into the ALN using ultrasound image guidance and were detected by bioluminescence. MamAb-680 was delivered by MFP injection and was observed to have traversed to the lymph node within 4 h. Fluorescence signal was retained in lymph nodes implanted with mammaglobin-A positive cells long after clearance from the MFP and negative lymph nodes. Positive lymph nodes were resolved as early as 4 h and were detected up to at least 7 days post-injection. These results show that in vivo lymphatic imaging using MamAb-680 provided a specific and durable signal in mammaglobin-A expressing lymph node metastases.

As a control, animals were injected with PBS and Matrigel (no cells) into the ALN using the same method and amounts used above, then injected MamAb-680 into the MFP and imaged. Minimal signal was detected in the draining lymphatics at 4 h post-injection and no signal was observed at 24 h. At 48 h, agent was cleared from the animal.

Figure 8A:
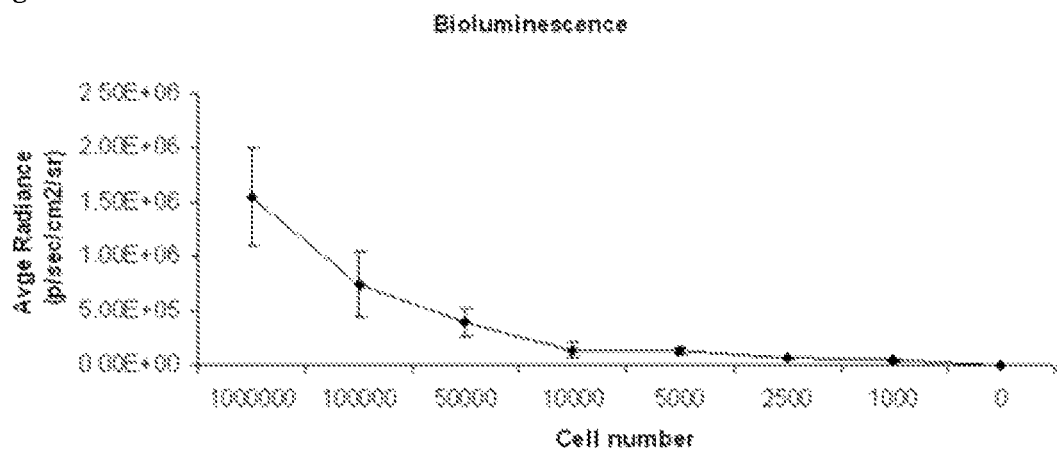
FIGS. 8A is a graphs showing bioluminescence (average radiance (photons/sec/cm$^2$/steradian)) of ZR-75.1/luc cells injection into MFP of ALN estrogen-pelleted mice as a function of the number of cells injected (1,000,000, 100,000, 10,000, 5,000, 1,000, or 0).
Figure 8B:
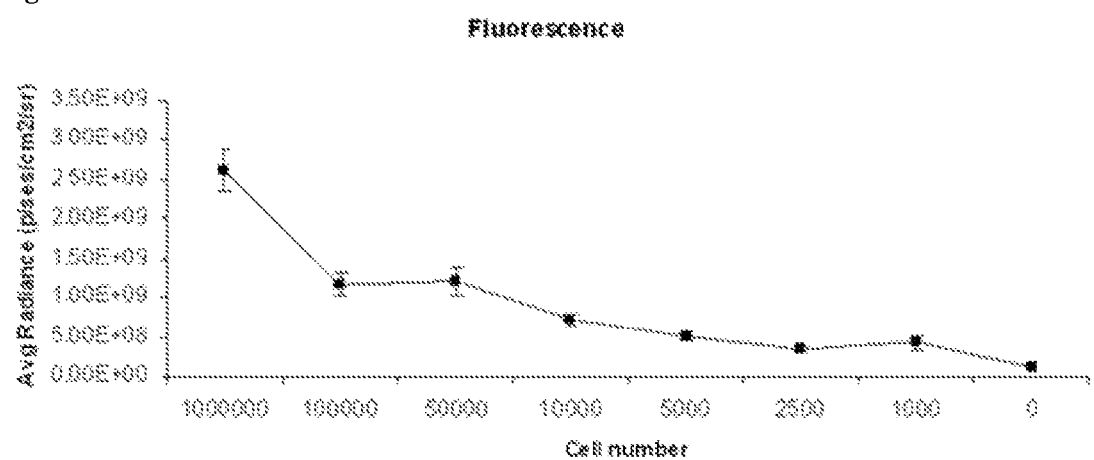
FIGS. 8B is a graph showing fluorescence (average radiance photons/sec/cm$^2$/steradian) 24 hours after injection of MamAb-680 into MFP of the mice of FIG. 8A as a function of the number (1,000,000, 100,000, 10,000, 5,000, 1,000, or 0) of ZR-75.1/luc cells injected into ALN. All data represent mean±s.d. of pixel values within the ROIs.

To determine the sensitivity of the agent, a range in number of ZR-75.1/luc (1000 to 1 million) were injected into ALN via ultrasound guidance. For confirmation of successful cell implantation, bioluminescence images were acquired and as few as 1,000 cells (FIG. 8A) detected. Four hours after cell injection, MamAb-680 were injected into mammary fat pad proximal to the ALN and acquired fluorescence images 24 h after injection (FIG. 8B) and bioluminescent and fluorescent signals quantified by drawing a region-of-interest (ROI) encompassing the tumor cells in the ALN. Signal intensity decreased with cell number and at least 1,000 cells were detectable above background (FIG. 8B).

Mammaglobin is expressed in malignant breast tissues and is not expressed in normal lymph node (LN) or skin, as determined by DNA and tissue microarray. A mammaglobin targeted imaging probe has therefore been developed. Three monoclonal antibodies (mAbs) were compared by immunostaining of cells, tissues and Western analysis. One highly specific mAb was conjugated to a near-infrared dye (VivoTag 680, VisEn) and intravenously injected into nude mice bearing bilateral mammary fat pad (MFP) tumors of mammaglobin-positive (ZR-75.1) and mammaglobin-negative (MDA-mb-231) cells. In vivo fluorescence imaging showed agent was retained only in ZR-75.1 tumors. Selectivity for positive LNs was determined by implanting ZR-75.1/luc cells in the axillary LN using ultrasound guidance and monitoring by bioluminescence Labeled mAb was delivered by MFP injection and traversed to LN. Label was retained in mammaglobin-positive LNs long after clearance from the MFP and negative LNs.

Example 14

Combination with Other Antibodies

Materials and Methods

DNA microarray analysis: Affymetrix expression data for the mammaglobin-A gene (SCGB2A2) in patient tissue samples were compiled from publicly available datasets. The CEL files for the tumor samples were downloaded from the NCBI Gene Expression Omnibus (GEO) database (ncbi.nlm.nih.gov/projects/geo/index.cgi), data series GSE2109. Normal tissue data were from the GEO data series GSE7307, Human Body Index. The CEL files were processed using the MAS 5.0 algorithm (Affymetrix, Santa Clara, Calif.) and screened through a rigorous quality control panel to remove samples with a low percentage of probesets called present by the MAS 5 algorithm, indicating problems with the amplification process or poor sample quality; high scaling factors, indicating poor transcript abundance during hybridization; and poor 3'/5' ratios, indicating RNA degradation either prior to or during processing. The remaining samples were normalized to the trimmed average of 500 in the MAS 5 algorithm before comparison of the expression values across tumors and normal samples.

Immunohistochemistry (IHC) of Tissue Mircroarray (TMA): A TMA was constructed at the Moffitt Tissue Core, containing 50 normal breast tissue, 50 ductal carcinoma in situ, 50 invasive ductal carcinomas without metastasis, 50 invasive ductal carcinomas with metastasis and 50 lymph node with macrometastases of breast carcinoma. The same method was previously reported by our group for construction of a Ewing sarcoma TMA (Sharma, P. et al. *Chem Mater* 20:6087-6094 (2008)), except the breast TMA has only one sample per case. Mouse anti-mammaglobin-A mAb, 1:50, (Clone 304-1 A5, Thermo Scientific, Rockford, Ill.) was used for staining Positive staining was arbitrarily set as membranous (partial or complete) and cytoplasmic immunoreactivity in greater than or equal to 5% of tumor cells. Results were recorded as positive or negative.

Statistics: Data are represented as mean±s.d. and the t-test was used to determine significance.

Results

To identify more targets, 3800 cell surface genes were curated from Gene Bank and used to filter DNA microarray data from 304 breast tumors (38 node positive), 111 normal breast tissues, 15 LNs, and 189 samples from 6 unaffected organ sites in the area surrounding the LNs and involved in clearance and toxicity. Of all genes, CA-9 and CA-12 were seen to be highly expressed in breast and LN-positive cancers but not in the normal tissues. Immunohistochemistry was performed on 50 normal breast tissues, 50 DCIS, 50 IDCs without metastasis, 50 IDCs with metastasis and 50 LN macrometastases. Nearly all (95%) of LN metastases expressed either CAIX or CAXII (Table 2). Thus, these CAs are valid targets for imaging of LN status for breast cancer.

TABLE 2

Coverage of breast cancer samples in the Moffitt breast cancer tissue microarray, including LN metastases, by three cell-surface markers, individually and in combination.

|  | Mammaglobin | CA9 | CA12 | Combination |
|---|---|---|---|---|
| DCIS | 80.0% | 71.4% | 81.3% | 100% (n = 9) |
| IDC without Mets | 53.1% | 55.8% | 78.7% | 100% (n = 28) |
| IDC with Mets | 42.9% | 56.5% | 80.4% | 93% (n = 26) |
| LN Macro Mets | 45.2% | 71.4% | 75.5% | 100% (n = 31) |

Note that the three markers, mammaglobin, CA9 and CA12 cover 100% of the lymph node metastases (n = 51) on the tissue microarray Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A non-invasive method for in vivo detection of metastasized breast cancer cells in a subject, the method comprising the steps of:
   (a) administering to the subject a first targeted imaging probe and a second targeted imaging probe,
   wherein the targeted imaging probes each comprise an antibody linked to a NIR fluorophore, wherein the antibody of the first imaging probe specifically binds carbonic anhydrase 9 (CAIX), wherein the antibody of the second imaging probe specifically binds carbonic anhydrase 12 (CAXII); and
   (b) imaging the subject with a molecular imaging device to detect the targeted imaging probes in the subject,
   wherein detection of the targeted imaging probes in an organ or a tissue of the subject is an indication of metastasized breast cancer cells in the organ or the tissue.

2. The method of claim 1, wherein the antibody that specifically binds CAIX is monoclonal antibody clone 303123 and the antibody that specifically binds CAXII is monoclonal antibody clone 315602.

3. A non-invasive method for intraoperative detection of metastasized breast cancer cells in a subject, the method comprising the steps of:
   (a) administering to the subject a first targeted imaging probe and a second targeted imaging probe,
   wherein the targeted imaging probes each comprise an antibody linked to a near-infrared (NIR) fluorophore, and
   wherein the antibody of the first targeted imaging probe specifically binds carbonic anhydrase 9 (CAIX),
   wherein the antibody of the second targeted imaging probe specifically binds carbonic anhydrase 12 (CAXII); and
   (b) imaging the subject with a molecular imaging device to detect the targeted imaging probes in the subject,
   wherein detection of the targeted imaging probes in an organ or a tissue of the subject is an indication of metastasized breast cancer cells in the organ or the tissue.

4. The method of claim 3, wherein the antibody that specifically binds CAIX is monoclonal antibody clone 303123.

5. The method of claim 3, wherein the antibody that specifically binds CAXII is monoclonal antibody clone 315602.

6. The method of claim 3, wherein the antibody that specifically binds CAIX is monoclonal antibody clone 303123, and wherein the antibody that specifically binds CAXII is monoclonal antibody clone 315602.

7. The method of claim 3 further comprising removing the metastasized breast cancer cells identified via the imaging from the organ or the tissue of the subject.

8. The method of claim 3 further comprising treating the subject for cancer if the imaging indicates the presence of metastasized breast cancer cells.

9. The method of claim 8 further comprising repeating the steps of claim 1 following treatment.

10. The method of claim 3, wherein the metastasized breast cancer cells are breast cancer cells metastasized to one or more lymph nodes.

11. The method of claim 10, wherein the one or more lymph nodes are axillary lymph node and/or sentinel lymph nodes.

* * * * *

UNITED STATES PATENT AND TRADEMARK OFFICE
CERTIFICATE OF CORRECTION

PATENT NO. : 11,077,212 B2
APPLICATION NO. : 13/813605
DATED : August 3, 2021
INVENTOR(S) : David L. Morse et al.

Page 1 of 1

It is certified that error appears in the above-identified patent and that said Letters Patent is hereby corrected as shown below:

In the Specification

Column 5, Line 30, please replace the term "FIGS" with "FIG".
Column 5, Line 30, please replace the term "graphs" with "graph".
Column 5, Line 34, please replace the term "FIGS" with "FIG".
Column 12, Line 17, please replace the phrase "1010 to 1020" with "$10^{10}$ to $10^{20}$".
Column 12, Line 17, please replace the term "oligonucleotide" with "oligonucleotides".
Column 12, Lines 18-19, please replace the term "oligonucleotide" with "oligonucleotides".
Column 13, Line 17, please replace the phrase "techniques is known" with "techniques known".
Column 15, Line 7, please replace the phrase "containing a pharmaceutical" with "containing pharmaceutical".
Column 15, Line 9, please replace the phrase "containing a one" with "containing one".
Column 33, Line 36, please replace the phrase "staining Positive" with "staining. Positive".

In the Claims

Claim 1, Column 35, Line 33, please replace the phrase "a NIR fluorophore" with "a near-infrared (NIR) fluorophore".
Claim 9, Column 36, Line 51, please replace the term "claim 1" with "claim 3".
Claim 11, Column 36, Line 56, please replace the term "node" with "nodes".

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 4

<210> SEQ ID NO 1
<211> LENGTH: 22
<212> TYPE: DNA
<213> ORGANISM: Artificial Sequence
<220> FEATURE:
<223> OTHER INFORMATION: synthetic construct; primer for CA12

<400> SEQUENCE: 1
ctggcatcat gtatttaggg gc                                      22

<210> SEQ ID NO 2
<211> LENGTH: 20
<212> TYPE: DNA
<213> ORGANISM: Artificial Sequence
<220> FEATURE:
<223> OTHER INFORMATION: synthetic construct; primer for CA12

<400> SEQUENCE: 2

-continued

```
gagttgcgcc tgtcagaaac                                              20

<210> SEQ ID NO 3
<211> LENGTH: 24
<212> TYPE: DNA
<213> ORGANISM: Artificial Sequence
<220> FEATURE:
<223> OTHER INFORMATION: synthetic construct; primer for Mammaglobin-A

<400> SEQUENCE: 3
cttcttcaag agttcataga cgac                                         24

<210> SEQ ID NO 4
<211> LENGTH: 22
<212> TYPE: DNA
<213> ORGANISM: Artificial Sequence
<220> FEATURE:
<223> OTHER INFORMATION: synthetic construct; primer for Mammaglobin-A

<400> SEQUENCE: 4
tgctcagagt ttcatccgtt tg                                           22
```